(12) United States Patent
Rajpara et al.

(10) Patent No.: US 10,350,047 B2
(45) Date of Patent: Jul. 16, 2019

(54) METHOD AND SYSTEM FOR PACKAGING AND PREPARING A PROSTHETIC HEART VALVE AND ASSOCIATED DELIVERY SYSTEM

(71) Applicant: Edwards Lifesciences Corporation, Irvine, CA (US)

(72) Inventors: Vipul P. Rajpara, Lake Forest, CA (US); Darshin S. Patel, San Juan Capistrano, CA (US); Michael R. Bialas, Lake Forest, CA (US); Brian R. Lowry, Fullerton, CA (US); Russ Hunton, Newport Beach, CA (US); Arvin T. Chang, Yorba Linda, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 142 days.

(21) Appl. No.: 15/250,759

(22) Filed: Aug. 29, 2016

(65) Prior Publication Data

US 2017/0056149 A1 Mar. 2, 2017

Related U.S. Application Data

(60) Provisional application No. 62/213,536, filed on Sep. 2, 2015.

(51) Int. Cl.
*A61F 2/24* (2006.01)
*A61F 2/00* (2006.01)
(Continued)

(52) U.S. Cl.
CPC .......... *A61F 2/0095* (2013.01); *A61F 2/2427* (2013.01); *B65D 1/34* (2013.01);
(Continued)

(58) Field of Classification Search
CPC .......... A61F 2/0095; A61F 2/24; B65D 1/34; B65D 77/26; A61M 5/002; A61B 2050/005
(Continued)

(56) References Cited

U.S. PATENT DOCUMENTS

| | | | |
|---|---|---|---|
| 4,011,947 A | 3/1977 | Sawyer | |
| 4,012,472 A * | 3/1977 | Lindsey | A61M 11/06 128/200.13 |

(Continued)

FOREIGN PATENT DOCUMENTS

| | | |
|---|---|---|
| CA | 2767527 A1 | 1/2011 |
| EP | 2218403 A1 | 8/2010 |

(Continued)

*Primary Examiner* — Steven A. Reynolds
(74) *Attorney, Agent, or Firm* — Hans P. Smith

(57) ABSTRACT

A packaging system for storing a prosthetic valve and an elongated delivery system in a non-fluid environment. The packaging system includes a tray for securing both a prosthetic valve and an elongated delivery system. The tray includes a cavity sized and shaped to house a valve cover containing the prosthetic valve and at least part of the distal portion of the elongated delivery system. A mounting surface removably couples the valve cover to the cavity floor and to prevent the valve cover from moving. An engaging surface is disposed peripherally of the cavity and is elevated above the cavity floor. A ramp extends downwardly from the engaging surface and into the cavity through an opening defined in the peripheral side wall and adjacent the floor of the cavity. The engaging surface and ramp are configured to secure at least part of the elongated delivery system externally of the cavity.

26 Claims, 21 Drawing Sheets

(51) Int. Cl.
*B65D 1/34* (2006.01)
*B65D 77/26* (2006.01)
*B65D 43/02* (2006.01)

(52) U.S. Cl.
CPC ............ *B65D 43/02* (2013.01); *B65D 77/26* (2013.01); *A61F 2/2412* (2013.01); *A61F 2240/001* (2013.01)

(58) Field of Classification Search
USPC ........................................ 206/364, 363, 438
See application file for complete search history.

(56) References Cited

U.S. PATENT DOCUMENTS

| | | |
|---|---|---|
| 4,101,031 A | 7/1978 | Cromie |
| 4,182,446 A | 1/1980 | Penny |
| 4,211,325 A | 7/1980 | Wright |
| 4,216,860 A * | 8/1980 | Heimann ............ A61M 25/002 206/364 |
| 4,697,703 A | 10/1987 | Will |
| 4,779,727 A * | 10/1988 | Taterka ............... A61M 25/002 206/364 |
| 4,801,015 A | 1/1989 | Lubock et al. |
| 5,098,391 A * | 3/1992 | Pantages ................ A61B 50/33 206/563 |
| 5,167,223 A | 12/1992 | Koros et al. |
| 5,236,450 A | 8/1993 | Scott |
| 5,336,616 A | 8/1994 | Livesey et al. |
| 5,392,918 A | 2/1995 | Harrison |
| 5,480,425 A | 1/1996 | Ogilive |
| 5,531,785 A | 7/1996 | Love et al. |
| 5,560,487 A | 10/1996 | Starr |
| 5,578,076 A | 11/1996 | Krueger et al. |
| 5,582,607 A | 12/1996 | Lackman |
| 5,615,770 A | 4/1997 | Applebaum et al. |
| 5,690,226 A | 11/1997 | N'Guyen |
| 5,720,391 A | 2/1998 | Dohm et al. |
| 5,776,187 A | 7/1998 | Krueger et al. |
| 5,800,531 A | 9/1998 | Cosgrove et al. |
| 5,823,342 A | 10/1998 | Caudillo et al. |
| 5,848,691 A * | 12/1998 | Morris ................. A61M 25/002 206/364 |
| 5,868,253 A | 2/1999 | Krueger et al. |
| 5,947,284 A * | 9/1999 | Foster .................... A61B 50/33 206/364 |
| 5,980,569 A | 11/1999 | Scirica |
| 5,984,959 A | 11/1999 | Robertson et al. |
| 6,040,416 A | 3/2000 | Sekharipuram et al. |
| 6,068,121 A * | 5/2000 | McGlinch ............ A61M 25/002 206/364 |
| 6,090,138 A | 7/2000 | Chasak et al. |
| 6,126,007 A | 10/2000 | Kari et al. |
| 6,197,053 B1 | 3/2001 | Cosgrove et al. |
| 6,199,696 B1 | 3/2001 | Lytle et al. |
| 6,346,094 B2 | 2/2002 | West et al. |
| 6,416,547 B1 | 7/2002 | Erickson et al. |
| 6,534,004 B2 | 3/2003 | Chen et al. |
| 6,591,998 B2 | 7/2003 | Haynes et al. |
| D480,816 S * | 10/2003 | McMichael .................. D24/227 |
| 6,723,122 B2 | 4/2004 | Yang et al. |
| 6,736,845 B2 | 5/2004 | Marquez et al. |
| 6,966,925 B2 | 11/2005 | Stobie |
| 7,000,770 B2 | 2/2006 | Clarke et al. |
| 7,389,874 B2 | 6/2008 | Quest et al. |
| 7,549,270 B2 | 6/2009 | Rowe et al. |
| 7,699,168 B2 | 4/2010 | Ryan et al. |
| 7,712,606 B2 | 5/2010 | Salahieh et al. |
| 7,749,266 B2 | 7/2010 | Forster et al. |
| 7,780,726 B2 | 8/2010 | Seguin |
| 7,866,468 B2 | 1/2011 | Kyritsis |
| 7,967,138 B2 | 6/2011 | Ryan et al. |
| 7,993,394 B2 | 8/2011 | Hariton et al. |
| 8,182,530 B2 | 5/2012 | Huber |
| 8,584,849 B2 * | 11/2013 | McCaffrey .......... A61M 25/002 206/364 |
| 8,652,145 B2 | 2/2014 | Maimon et al. |
| 8,652,202 B2 | 2/2014 | Alon et al. |
| 8,801,776 B2 | 8/2014 | House et al. |
| 9,155,619 B2 | 10/2015 | Liu et al. |
| 9,168,131 B2 | 10/2015 | Yohanan et al. |
| 9,867,700 B2 | 1/2018 | Bakis et al. |
| 2002/0032481 A1 | 3/2002 | Gabbay |
| 2002/0120328 A1 | 8/2002 | Pathak et al. |
| 2002/0151970 A1 | 10/2002 | Garrison et al. |
| 2002/0161377 A1 | 10/2002 | Rabkin |
| 2003/0040792 A1 | 2/2003 | Gabbay |
| 2003/0070944 A1 | 4/2003 | Nigam |
| 2003/0213715 A1 | 11/2003 | Klepac et al. |
| 2004/0210304 A1 | 10/2004 | Seguin et al. |
| 2004/0236411 A1 | 11/2004 | Sarac et al. |
| 2004/0243214 A1 * | 12/2004 | Farrell ................. A61F 2/0095 623/1.11 |
| 2004/0260308 A1 | 12/2004 | Gilson et al. |
| 2005/0075173 A1 | 4/2005 | Artof et al. |
| 2005/0113910 A1 | 5/2005 | Paniagua et al. |
| 2005/0137688 A1 | 6/2005 | Salahieh et al. |
| 2005/0137693 A1 | 6/2005 | Haug et al. |
| 2005/0137697 A1 | 6/2005 | Salahieh et al. |
| 2005/0149159 A1 | 7/2005 | Andreas et al. |
| 2005/0241981 A1 | 11/2005 | Gupta et al. |
| 2006/0149360 A1 | 7/2006 | Schwammenthal et al. |
| 2006/0155363 A1 | 7/2006 | LaDuca et al. |
| 2006/0195183 A1 | 8/2006 | Navia et al. |
| 2006/0259136 A1 | 11/2006 | Nguyen et al. |
| 2006/0276613 A1 | 12/2006 | Greenberg |
| 2006/0282045 A1 * | 12/2006 | Wilkinson ............. A61B 5/417 604/198 |
| 2006/0287719 A1 | 12/2006 | Rowe et al. |
| 2007/0073389 A1 | 3/2007 | Bolduc et al. |
| 2007/0084144 A1 | 4/2007 | Labrecque et al. |
| 2007/0088431 A1 | 4/2007 | Bourang et al. |
| 2007/0213813 A1 | 9/2007 | Von Segesser et al. |
| 2008/0023346 A1 | 1/2008 | Vonderwalde |
| 2008/0082163 A1 | 4/2008 | Woo |
| 2008/0177381 A1 | 7/2008 | Navia et al. |
| 2008/0319526 A1 | 12/2008 | Hill et al. |
| 2009/0099638 A1 | 4/2009 | Grewe |
| 2009/0130162 A2 | 5/2009 | Pathak et al. |
| 2009/0164005 A1 | 6/2009 | Dove et al. |
| 2010/0049313 A1 | 2/2010 | Alon et al. |
| 2010/0191326 A1 | 7/2010 | Alkhatib |
| 2010/0219092 A1 | 9/2010 | Salahieh et al. |
| 2011/0040374 A1 | 2/2011 | Goetz et al. |
| 2011/0147251 A1 | 6/2011 | Hodshon et al. |
| 2012/0071969 A1 | 3/2012 | Li et al. |
| 2012/0103840 A1 | 5/2012 | McCaffrey |
| 2012/0158128 A1 | 6/2012 | Gautam et al. |
| 2012/0305441 A1 | 12/2012 | Murray et al. |
| 2013/0123914 A1 | 5/2013 | Fish et al. |
| 2013/0206634 A1 | 8/2013 | Tijssen |
| 2013/0325111 A1 | 12/2013 | Campbell et al. |
| 2014/0202908 A1 | 7/2014 | Liburd et al. |
| 2014/0216955 A1 | 8/2014 | Murray et al. |
| 2015/0157455 A1 | 6/2015 | Hoang et al. |
| 2016/0213441 A1 | 7/2016 | Connolly |
| 2017/0056149 A1 | 3/2017 | Rajpara et al. |
| 2017/0128197 A1 | 5/2017 | Bialas et al. |
| 2017/0156839 A1 | 6/2017 | Cooper et al. |
| 2017/0156859 A1 | 6/2017 | Chang et al. |
| 2017/0231765 A1 | 8/2017 | Desrosiers et al. |
| 2017/0258584 A1 | 9/2017 | Chang et al. |

FOREIGN PATENT DOCUMENTS

| | | |
|---|---|---|
| WO | 9951167 A2 | 10/1999 |
| WO | 0041652 A1 | 7/2000 |
| WO | 2008035337 A2 | 3/2008 |
| WO | 2008124844 A1 | 10/2008 |
| WO | 2012150290 A1 | 11/2012 |

* cited by examiner

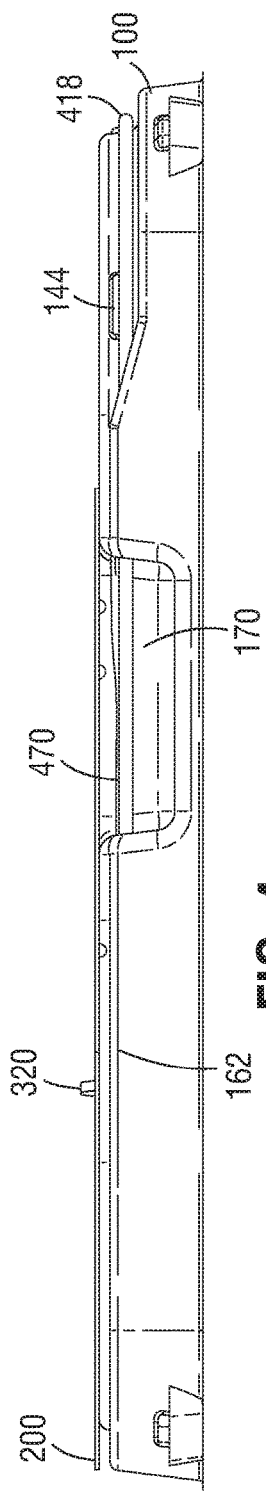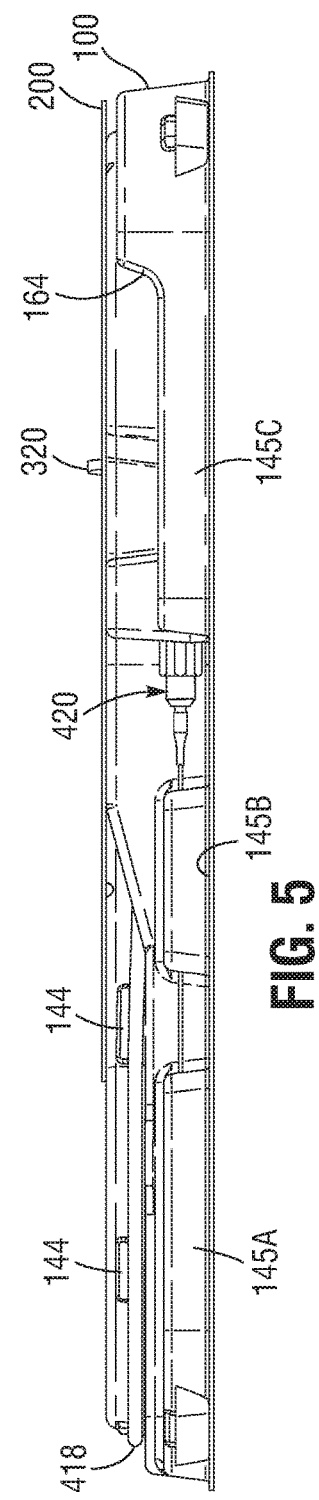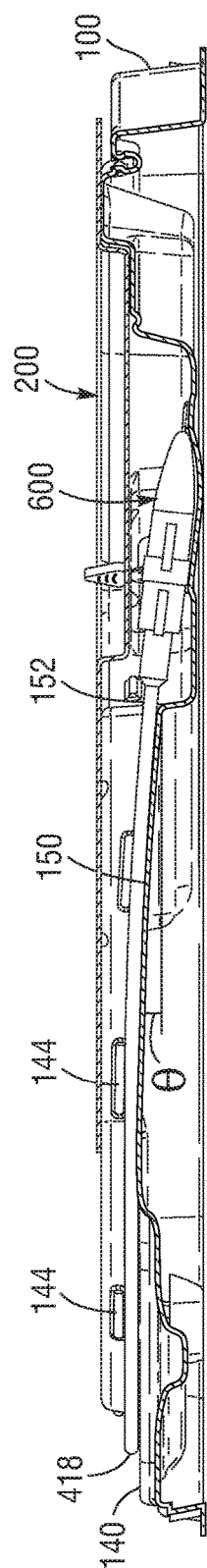

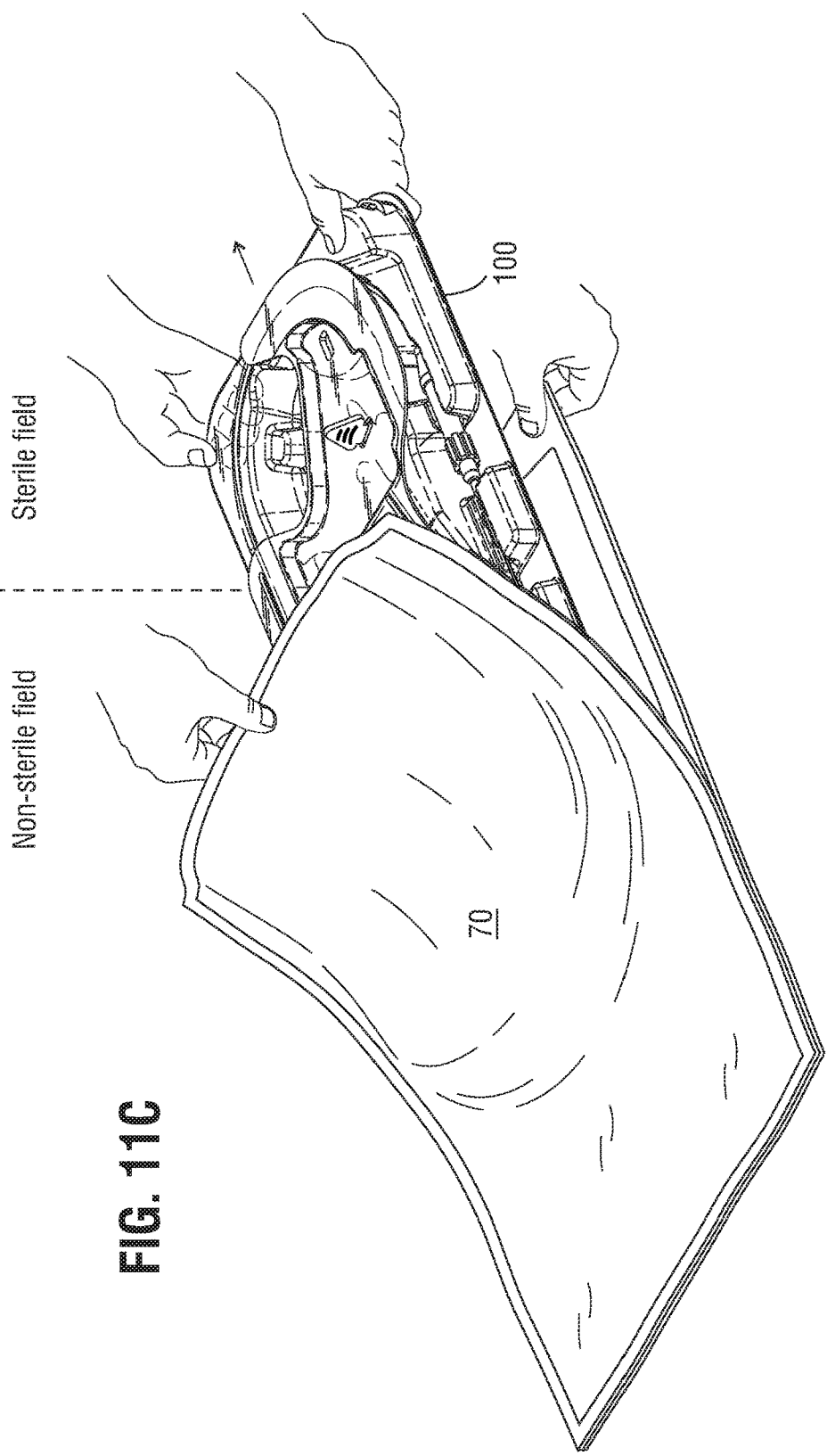

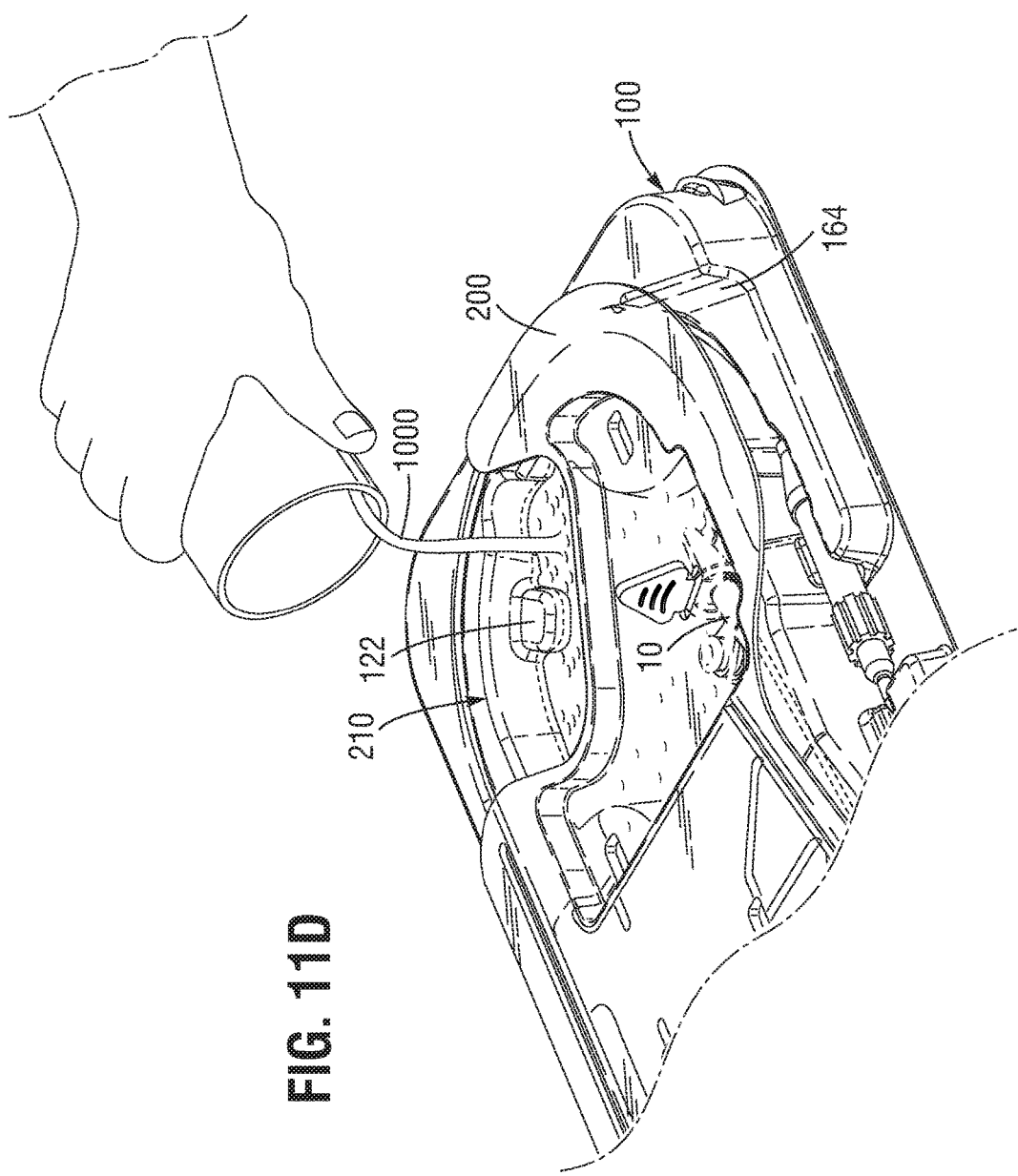

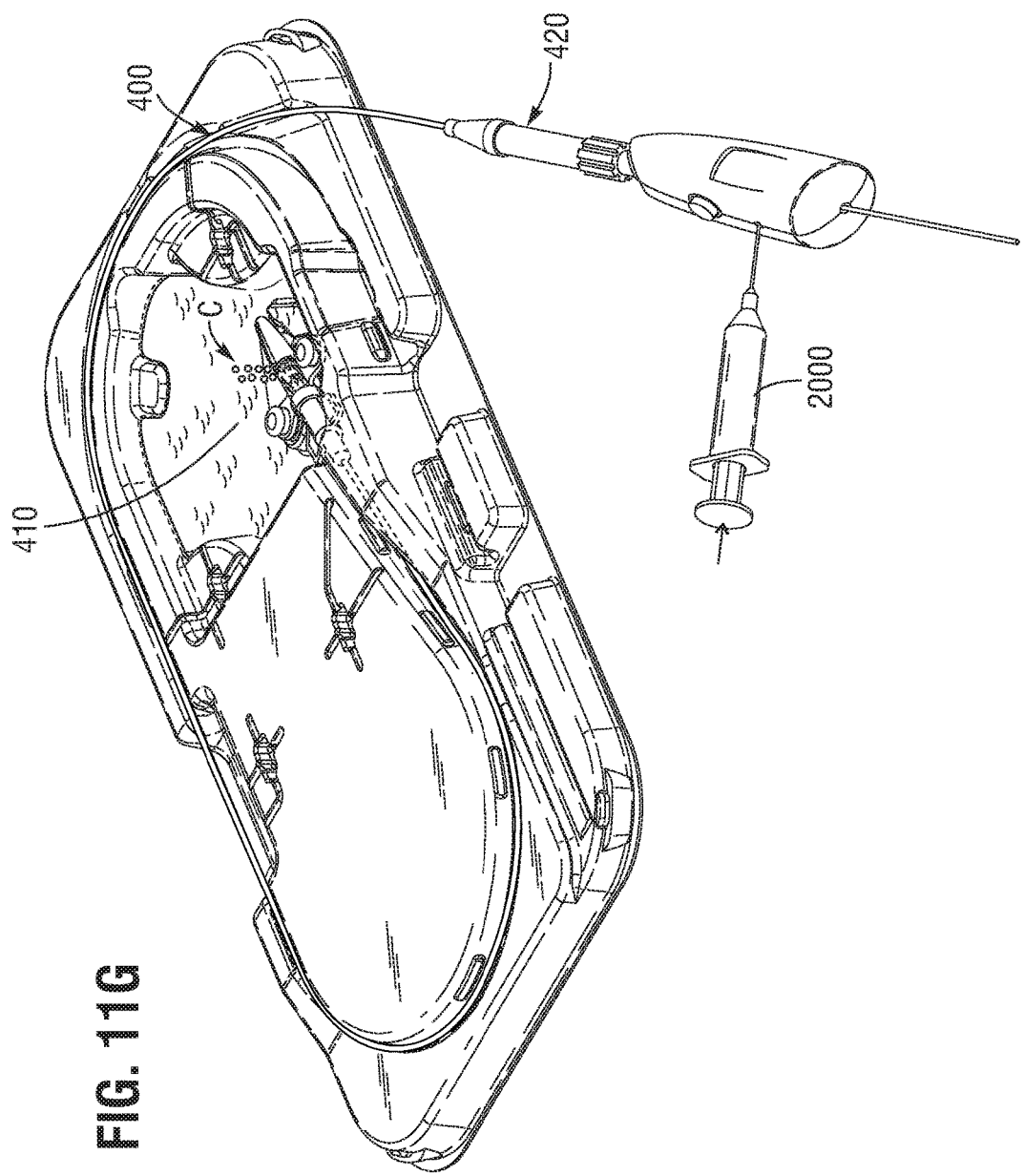

ual METHOD AND SYSTEM FOR PACKAGING AND PREPARING A PROSTHETIC HEART VALVE AND ASSOCIATED DELIVERY SYSTEM

CROSS-REFERENCE TO RELATED APPLICATION

This applications claims the benefit of priority under 35 U.S.C. § 119 of U.S. Provisional Patent Application Ser. No. 62/213,536, filed Sep. 2, 2015, the entire contents of which are incorporated herein by reference.

FIELD OF THE INVENTION

This invention relates to a packaging for medical devices and, more particularly, to a method and system for packaging and preparing a prosthetic valve and its associated delivery system.

BACKGROUND

There are at least two options for replacing a diseased heart valve: surgical valve replacement, which includes open heart surgery and minimal incision valve surgery, and transcatheter heart valve replacement. For certain high-risk patients, surgical valve replacement may not be appropriate due to its invasive nature and, for these patients, transcatheter heart valve replacement may be a viable alternative. Transcatheter heart valve replacement is less invasive and allows the replacement heart valve to be delivered through the patient's vasculature, typically through the femoral artery.

There is strong incentive for efficiency in the operating room since reducing operating room time reduces the amount of time a patient is under anesthesia and the overall costs to the doctor or hospital. Preparing a replacement heart valve and its associated delivery system, however, can be complicated and time-consuming. The steps for assembling the replacement heart valve on its delivery system for implantation must be followed precisely and in a specific order. Any deviation from the prescribed procedures may damage the replacement heart valve or compromise the proper functioning of its associated delivery device. Moreover, because the procedure typically requires the participation of several operating room attendants and doctors, across non-sterile and sterile fields, the possibility of human error or mistake is always present.

BRIEF SUMMARY

The packaging systems disclosed herein provide a platform for the compact storage and transportation of a replacement heart valve and its associated delivery system. The packaging systems also provide for the handling, preparation and assembly of the replacement heart valve and its associated delivery system in the operating room. The packaging system described herein provides a combination of features that facilitate this process in an efficient manner by reducing the number of steps and operating room personnel required to prepare and assemble the replacement heart valve onto its delivery system and also by ensuring that the steps are performed in the required sequence. The features of the packaging system also advantageously permit the prosthetic valve and associated delivery system to be secured in a compact configuration that allows for reduced overall dimensions of the packaging system.

It is understood that the packaging systems disclosed herein are not only suitable for the prosthetic valves and delivery systems specifically disclosed herein but also for other prosthetic valves and delivery systems, such as those disclosed in U.S. Pub. No. 2010/0049313, published Feb. 25, 2010; U.S. Pub, No. 2012/0239142, published Sep. 20, 2012, and U.S. Pub. No. 2014/0343670, published Nov. 20, 2014, the entire contents of each of which are incorporated herein by reference in its entirety.

A packaging system for storing a prosthetic valve and an elongated delivery system in a non-fluid environment is provided. The packaging system can comprise a tray that can secure both a prosthetic valve and an elongated delivery system. The prosthetic valve can be maintained in a compressed state around a distal portion of the elongated delivery system by a valve cover coupled to the prosthetic valve.

The tray can include a cavity having an open end, a floor, and a peripheral side wall defining a depth of the cavity. The cavity can be sized and shaped to house the valve cover and the prosthetic valve. The tray can also comprise an engaging surface peripherally of the cavity and elevated above the cavity floor.

A mounting surface can be provided to removably couple the valve cover to the cavity floor.

The tray can include a ramp extending downwardly from the engaging surface and into the cavity through an opening defined in the peripheral side wall and adjacent the floor of the cavity.

The engaging surface and the ramp can be configured to secure at least a portion of the elongated delivery system externally of the cavity.

In one optional embodiment, the prosthetic valve can comprises a stent and a plurality of leaflets coupled to the stent, the plurality of leaflets comprising a biological tissue.

In another optional embodiment, the engaging surface can comprise a channel formed in the tray and shaped to accommodate the elongated delivery system. The channel can comprise tabs to resiliently engage the elongated delivery system within the channel.

In a further optional embodiment, the ramp can be angled downwardly from the engaging surface to the floor of the cavity. The ramp can be provided at an angle of about 4 degrees to about 10 degrees relative to a horizontal plane bisecting the tray.

In yet another optional embodiment, the packaging system can comprise a lock configured to be removably coupled to one or both of the valve cover and the distal portion of the elongated delivery system. The packaging system can further comprise a lid removably coupled to the tray and partially enclosing the open end of the cavity. The lid can further define an opening to the cavity through which fluid can be poured into the cavity. The lock can comprise a first end and a second end. The first end of the lock can be removably coupled to one or both of the valve cover and the distal portion of the elongated delivery system. The second end can be configured to protrude externally of the cavity through an aperture disposed on the lid. The second end can be sized or shaped to prevent it from being passed through the aperture. Alternatively, the second end can be fixed to or integrated with the lid. In any of the foregoing embodiments, removing the lid can also remove the first end of the lock from the one or both of the valve cover and the elongated delivery system.

In yet a further optional embodiment, the valve cover can comprise an internal cavity. The internal cavity can be sized and dimensioned to house a nose piece, the prosthetic valve and part of the distal portion of the elongated delivery system. A lock can be provided that is removably coupled to both the valve cover and the distal portion of the elongated delivery system. A first end of the lock can be positioned to maintain a separation between the nose piece and the prosthetic valve.

In another optional embodiment, the valve cover can comprise wings extending laterally from opposing sides of the valve cover. The wings can be configured to couple the mounting surface disposed from the cavity floor. The mounting surface can be one of a pair of protrusions or a pair of recesses that are configured to mate with corresponding features of the wings. The corresponding features of the wings can be the other of the pair of protrusions or the pair of recesses. The wings and the mounting surface can be in resilient snap-fit engagement.

In a further optional embodiment, the cavity can further comprise a fill line disposed from the cavity peripheral side wall between the floor and the open end.

In yet another optional embodiment, a free segment of the elongated delivery system can be provided externally of the cavity and not in direct physical contact with the tray. A space can be provided around the free segment to permit a user's hand to grasp the free segment and to lift at least a portion of the elongated delivery system on both sides of the free segment out of engagement with the tray.

In yet a further optional embodiment, the proximal end of the elongated delivery device can be engaged within a periphery of the tray. The tray can comprise a support surface for maintaining the proximal end of the elongated delivery system in position for coupling the proximal end with a handle when the proximal end is disengaged from and extends externally away from the periphery of the tray.

In yet a further optional embodiment, the mounting surface can resiliently engage at least a portion of the valve cover. The valve cover can comprise a flared open end, an opposing securing end, and a lock ring mounted slidably around the securing end between a locked position and an unlocked position. In the locked position, the lock ring can exert a radially inward force around the securing end of the valve cover to secure the valve cover onto the delivery system. In the unlocked position, the radially inward force exerted by the lock ring can be released to permit removal of the delivery device from the valve cover. The lock ring can be housed within a spaced area of the mounting surface to permit the lock ring to slide between the locked and unlocked positions.

In yet a further optional embodiment, the lid can completely enclose the upper surface of the tray.

In yet a further optional embodiment, the packaging system can further comprise a handle attached to the delivery system and packaged within the tray.

A method for preparing a prosthetic valve and its associated delivery system for implantation of the prosthetic valve in a patient is also provided. The method can comprise any one or a combination of steps (a) through (e) as described below.

Step (a) can include obtaining a tray, the tray comprising a prosthetic valve in a first compressed state and coupled to an elongated delivery system.

In one optional embodiment, the tray can include a cavity comprising an open end, a floor, and a peripheral side wall defining a depth of the cavity. The cavity can be sized and shaped to house the prosthetic valve and at least part of a distal portion of the elongated delivery system. A mounting surface can be provided to substantially immobilize and maintain the prosthetic valve within the cavity. The tray can further include an engaging surface peripherally of the cavity, the engaging surface securing at least a part of the elongated delivery system externally of the cavity. In accordance with one aspect of this embodiment, the cavity does not comprise a liquid or a preservative solution.

Step (b) can include at least partially filing the cavity with a first hydrating fluid to completely immerse the prosthetic valve.

Step (c) can include allowing the prosthetic valve to soak in the first hydrating fluid for a period of time. In one embodiment, the period of time can be at least 5 minutes, at least 10 minutes, at least 15 minutes, at least 20 minutes, at least 25 minutes, or at least 30 minutes.

Step (d) can include flushing the elongated delivery system by delivering a second hydrating fluid into a proximal end of the elongated delivery system and causing the second hydrating fluid to pass through a lumen extending through the elongated delivery system and out of the distal portion of the elongated delivery system.

Step (e) can comprise causing the prosthetic valve to be loaded into a lumen of a delivery sheath associated with the elongated delivery system while the prosthetic valve is coupled to the cavity floor via the mounting surface. The loading can be performed by causing the delivery sheath to move axially over the prosthetic valve. The delivery sheath can compress and contain the prosthetic valve within a lumen of the delivery sheath in a second compressed state. A diameter of the prosthetic valve in the first compressed state can be larger than a diameter of the prosthetic valve in the second compressed state.

Step (f) can comprise removing the elongated delivery device with the prosthetic valve loaded into the lumen of the delivery sheath from the tray, including disengaging the prosthetic valve from the mounting surface.

In one optional embodiment, steps (a) through (e) can be performed while the prosthetic valve is substantially immobilized and maintained within the cavity.

The method can further comprising coupling a handle to the proximal end of the elongated delivery system after (a) and before (d).

A method for preparing a prosthetic valve and its associated delivery system for implantation of the prosthetic valve in a patient is also provided. The method can comprise any one or a combination of steps (a) through (e) as described below.

Step (a) can comprise obtaining a tray, the tray comprising a prosthetic valve in a first compressed state and coupled to an elongated delivery system.

In one optional embodiment, the tray can include a cavity comprising an open end, a floor, and a peripheral side wall defining a depth of the cavity. The cavity can be sized and shaped to house a valve cover comprising the prosthetic valve and at least part of a distal portion of the elongated delivery system. A mounting surface can be provided to substantially immobilize and maintain a valve cover coupled to a distal end of the elongated delivery system and the prosthetic valve within the cavity. An adjacent reservoir can be provided in fluid communication with the cavity. In accordance with one aspect of this embodiment, the cavity does not comprise a liquid or a preservative solution.

Step (b) can comprise at least partially filing the cavity with a first hydrating fluid until the first hydrating fluid overflows into the adjacent reservoir.

Step (c) can comprise flushing the elongated delivery system by delivering a second hydrating fluid through a first lumen extending through the elongated delivery system.

Step (d) can comprise causing the prosthetic valve to be loaded into a lumen of a delivery sheath associated with the elongated delivery system while the valve cover is coupled to the mounting surface. During loading, the delivery sheath can compress and contain the prosthetic valve within a lumen of the delivery sheath in a second compressed state. A diameter of the prosthetic valve in the first compressed state can be larger than a diameter of the prosthetic valve in the second compressed state.

Step (e) can comprise flushing the elongated delivery system by delivering a third hydrating fluid through a second lumen extending through the elongated delivery system.

Step (f) can comprise removing the elongated delivery device with the prosthetic valve loaded into the lumen of the delivery sheath from the valve cover and the tray.

Steps (a) through (e) can be performed while the valve cover is substantially immobilized and maintained within the cavity.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Preferred and non-limiting embodiments of the inventions may be more readily understood by referring to the accompanying drawings in which:

FIG. 4 is an elevation view of side 4-4 of the packaging system, prosthetic valve and associated delivery system of FIG. 3.

FIG. 5 is an elevation view of side 5-5 of the packaging system, prosthetic valve and associated delivery system of FIG. 3.

FIG. 6 is a cross-sectional view of the packaging system, prosthetic valve and associated delivery system taken along 6-6 of FIG. 3.

Like numerals refer to like parts throughout the several views of the drawings.

DETAILED DESCRIPTION OF THE EXEMPLARY EMBODIMENTS

Specific, non-limiting embodiments of the present invention will now be described with reference to the drawings. It should be understood that such embodiments are by way of example only and merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

FIGS. 1-6 illustrate an embodiment of the packaging system 1 comprising a prosthetic valve 10 and its associated delivery system 400 both packaged within a tray 100. Specific details of exemplary delivery systems that may be used in connection with the packaging system 1 disclosed herein can include those described in, e.g., U.S. Pub. No. 2010/0049313, filed Apr. 23, 2009; U.S. Pub. No. 2012/0239142, filed Feb. 24, 2012; and U.S. Pub. No. 2014/0343670, filed May 20, 2014. The entire contents of each of these references are incorporated herein in their entireties as if fully set forth herein. Of course, it is to be understood that other heart valves and delivery systems can also be used in the packaging system described herein.

Figure 7:
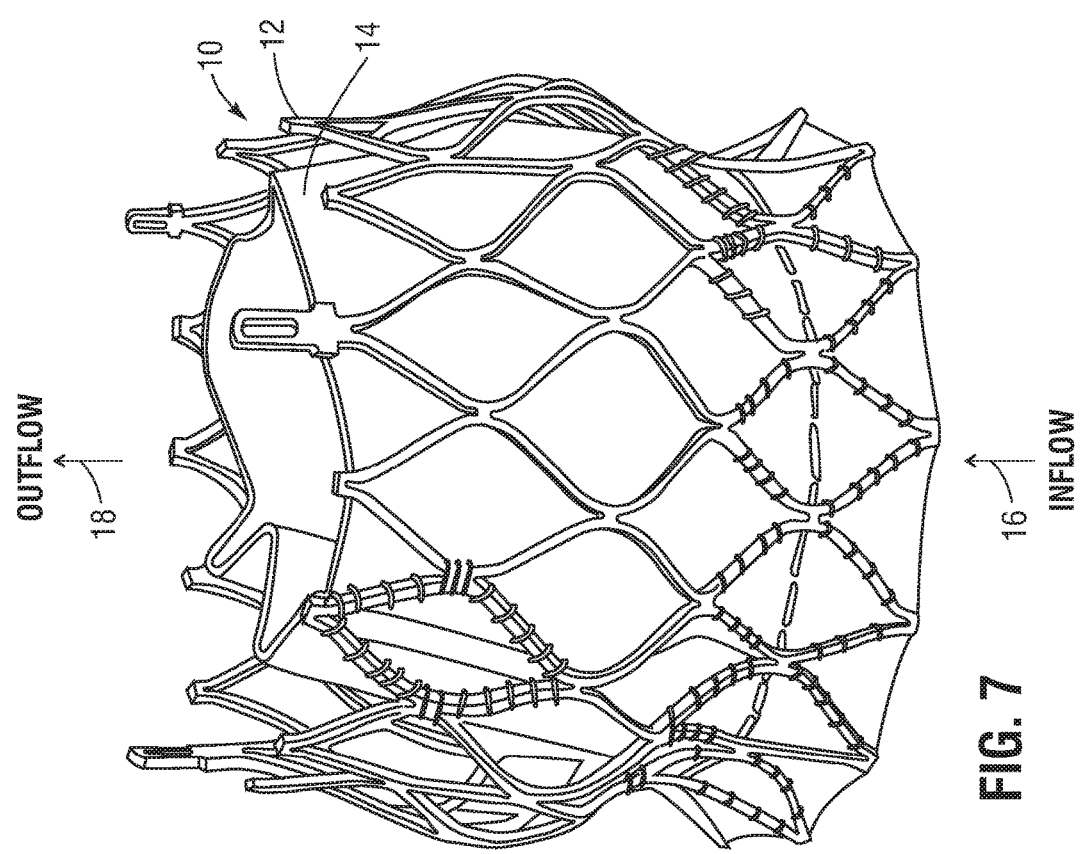
FIG. 7 is a perspective view of a prosthetic valve that can be used to replace a native aortic valve of the heart.

FIG. 7 depicts an exemplary prosthetic valve 10 having an inflow end 16 and an outflow end 18. The prosthetic valve 10 can include an expandable frame member or stent 12 that supports a flexible leaflet section 14. The flexible leaflet section 14 can comprise a biological tissue, such as pericardium, epidermis, blood vessels, skin, dura mater, small intestinal mucosa, tissue heart valves, ligaments, and tendons. In one embodiment, the foregoing biological tissue can be derived from animal sources, such as from bovine, equine, porcine, and kangaroo species. In another embodiment, the foregoing biological tissue can be derived from autologous or allogenic human sources. The biological tissue can be subjected to chemical or mechanical treatment such that it does not require immersion in a liquid preservative solution for storage and transportation. Exemplary methods for treating biological tissues are described in U.S. Pat. Nos. 7,972,376 and 8,007,992, the entire contents of which are incorporated herein by reference in their entireties. As noted above, it is to be understood that other heart valves and delivery systems can also be used in the packaging system described herein.

In one embodiment, the prosthetic valve 10 that is used in connection with the various embodiments of the packaging systems described herein comprise leaflets 14 comprising biological tissue and that have been at least partially dried or dehydrated to permit storage of the prosthetic valve 10 without immersion in a liquid or a preservative solution. In accordance with one aspect of the embodiment, the biological tissue leaflets 14 can be subjected to a chemical or mechanical treatment so as to reduce the water content about 50% by weight or less, 25% by weight or less, 10% by weight or less, 5% by weight or less, 2% by weight or less, 1% by weight or less, 0.5% by weight or less, 0.25% by weight or less, or 0.10% by weight or less of the total weight of the biological tissue leaflets 14. Additionally, the water content of the biological tissue leaflets 14 may be a range between and including any two of the foregoing values. The biological tissue leaflets 14 can comprise interstices within the tissue structure in which at least a portion of the water has been replaced with a different substance, such as a polyol or, more specifically, alcohol or glycerol. In accordance with another aspect of the embodiment, the biological tissue leaflets 14 may be completely dried or dehydrated, with the water content present in the tissue being no more than the amount attributable to the humidity of the ambient environment.

The prosthetic valve 10 can be deployed in the native aortic annulus, although it also can be used to replace other native valves of the heart or within the body, such as venous valves. Thus, it is understood that the prosthetic valve 10 can be a prosthetic heart valve, a prosthetic venous valve or other valve that may be implanted within a body cavity. The prosthetic valve 10 is radially compressible to a compressed state of a smaller diameter for delivery through the vasculature of the body and to a deployment site. Once the prosthetic valve 10 reaches its deployment site, it can be expanded to its functional size as shown in FIG. 7.

In certain embodiments, the prosthetic valve 10 can be self-expanding; that is, the prosthetic valve 10 can radially expand to its functional size when advanced from the distal portion 410 of a delivery system 400. In other embodiments, the prosthetic valve 10 can be balloon-expandable and can be adapted to be mounted in a compressed state on the balloon of an elongated delivery system 400. The prosthetic valve 10 can be expanded to its functional size at a deployment site by inflating the balloon which, in turn, expands the prosthetic valve 10 as known in the art. In still other embodiments, the prosthetic valve 10 can be mechanically expandable, relying on neither self-expansion nor a balloon to expand the valve to its functional size.

Figure 8A:
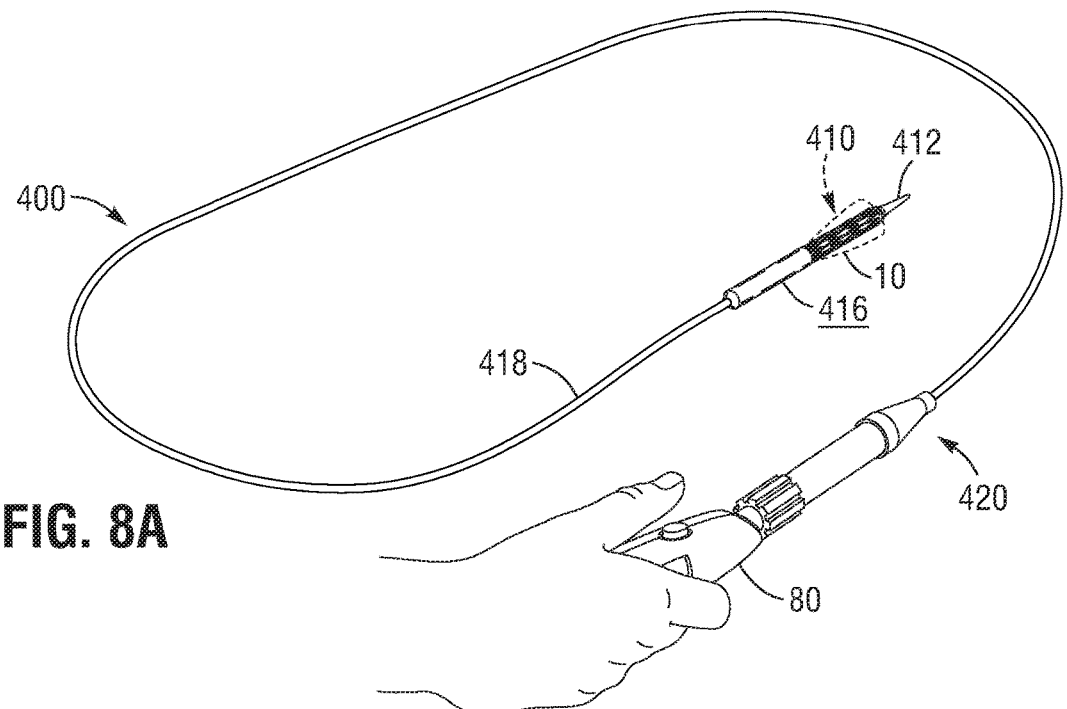
FIGS. 8A and 8B depict the actuation of the delivery sheath from an unloaded configuration to a loaded configuration, respectively. In the loaded configuration, the heart valve is contained within the delivery sheath.
Figure 8B:
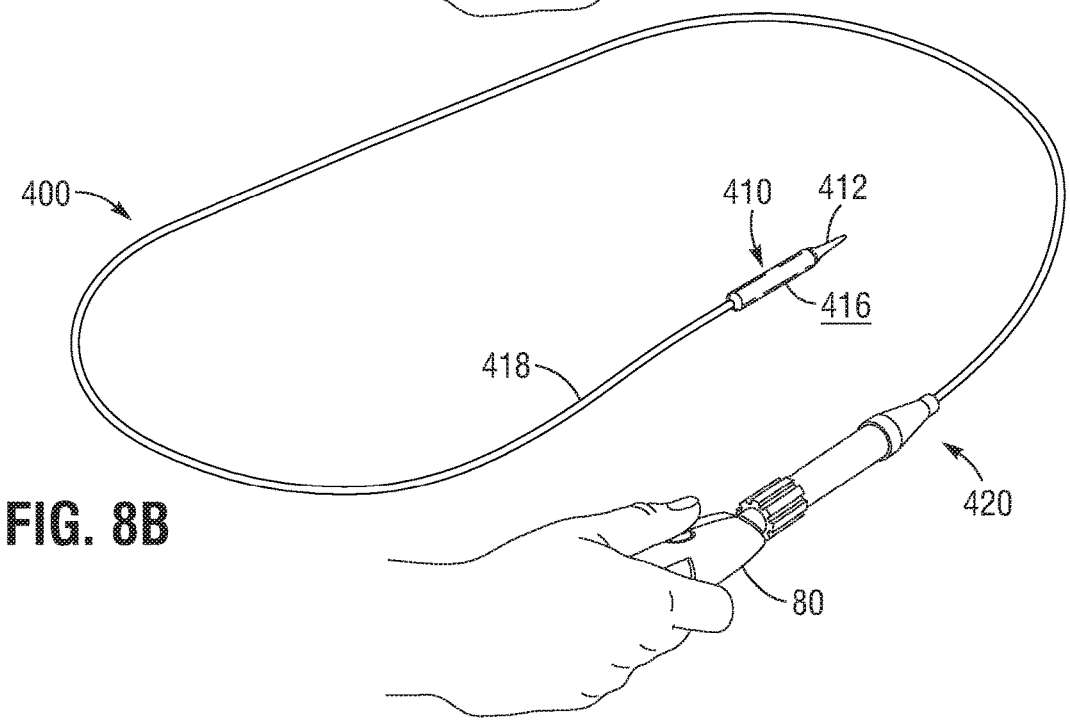

An exemplary delivery system 400 that can be stored in the tray 100 along with the prosthetic valve 10 is depicted in FIGS. 8A and 8B. The delivery system 400 can comprise a distal portion 410 onto which a prosthetic valve 10 is mounted and a proximal portion 420 onto which a handle 80 is attached.

The distal portion 410 of the delivery system 400 can comprise a nose piece 412 secured to the distal portion 410 of a shaft. The nose piece 412 can be shaped as a cone having a tapered outer surface for atraumatic tracking through the patient's vasculature. The shaft extends from the nose piece 412 through the prosthetic valve 10 and coaxially through a main catheter 418. The main catheter 418 has a distal end that is coupled to a delivery sheath 416 that is movable axially in either one of the distal and proximal directions. It is understood that a distal direction corresponds to a direction towards the nose piece 412 or away from a proximal portion 420 of the delivery catheter and a proximal direction corresponds to a direction away from the nose piece 412 or towards a proximal portion 420 of the delivery system 400. The shaft can optionally comprise a guide wire (not shown) so that the delivery system 400 can be advanced over the guide wire inside a patient's vasculature.

The proximal portion 420 of the delivery system 400 can be attached to a handle 80. The handle 80 can have an electric motor for operating the delivery apparatus and for actuating the delivery sheath 416 to move axially in distal and proximal directions by depressing a button, as shown in FIG. 8B. When the delivery sheath 416 is actuated to move in a distal direction, it will compress and contain the prosthetic valve 10 within the delivery sheath 416, as shown in FIG. 8B. When the delivery sheath 416 is actuated to move in a proximal direction, it will expose the prosthetic valve 10 from the delivery sheath 416 and permit it to assume an expanded configuration for implantation, as shown in FIG. 8A. The handle 80 can be provided separately from the packaging system 1.

Returning now to FIGS. 1-6, the tray 100 can store and transport the prosthetic valve 10 coupled to the delivery system 400. In one embodiment, the prosthetic valve 10 can be mounted around a portion of the shaft, substantially between the delivery sheath 416 and the nose piece 412. One end of the prosthetic valve 10 can be compressed and contained within the delivery sheath 416 and the remaining portion of the prosthetic valve 10 can be provided externally of and extending distally from the delivery sheath 416.

Having one end of the prosthetic valve 10 compressed and contained within the delivery sheath 416 facilitates loading of the prosthetic valve 10 within the delivery sheath 416. In one embodiment, a portion of the inflow end 14 is compressed and contained within the delivery sheath 416 and the outflow end extends distally from the delivery sheath 416. In another embodiment, a portion of the outflow end 16 is compressed and contained within the delivery sheath 416 and the inflow end extends distally from the delivery sheath 416.

The loading of the prosthetic valve 10 within the delivery sheath 416 can be accomplished in a number of ways. In one embodiment, the prosthetic valve 10 is loaded within the delivery sheath 416 by causing the prosthetic valve 10 to move in a proximal direction. In another embodiment, the prosthetic valve 10 is loaded within the delivery sheath 416 by causing the delivery sheath 416 to move in a distal direction.

Figure 9:
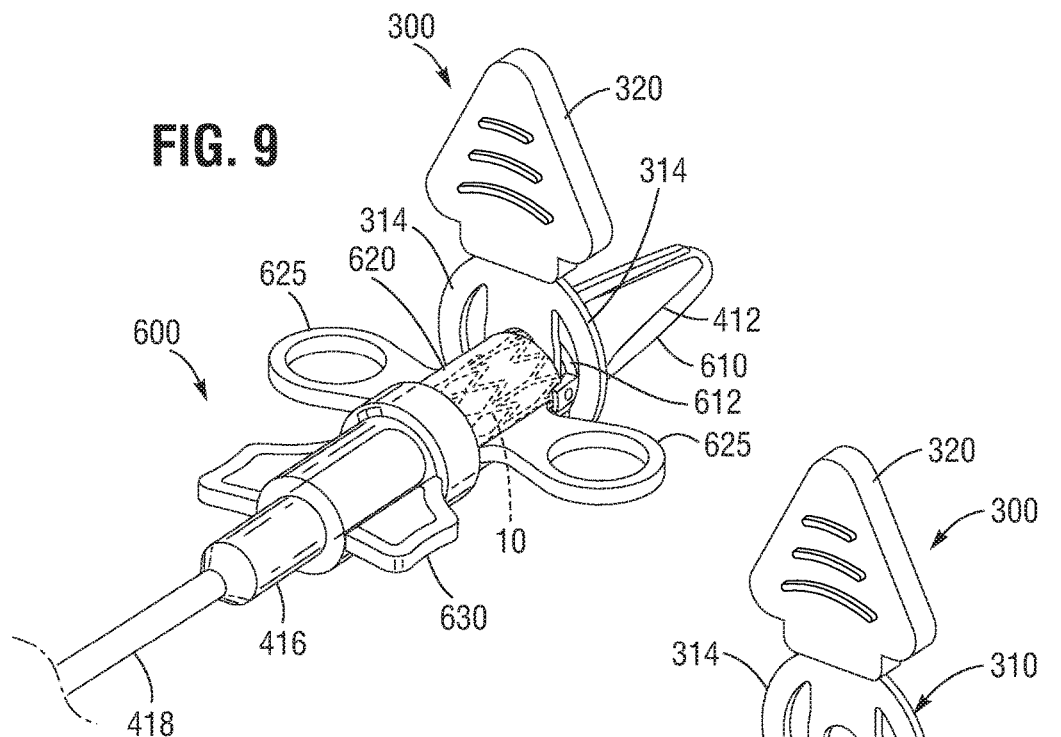
FIG. 9 depicts the distal portion of the delivery system including the heart valve, the valve cover and the lock in the assembled configuration.
Figure 10:
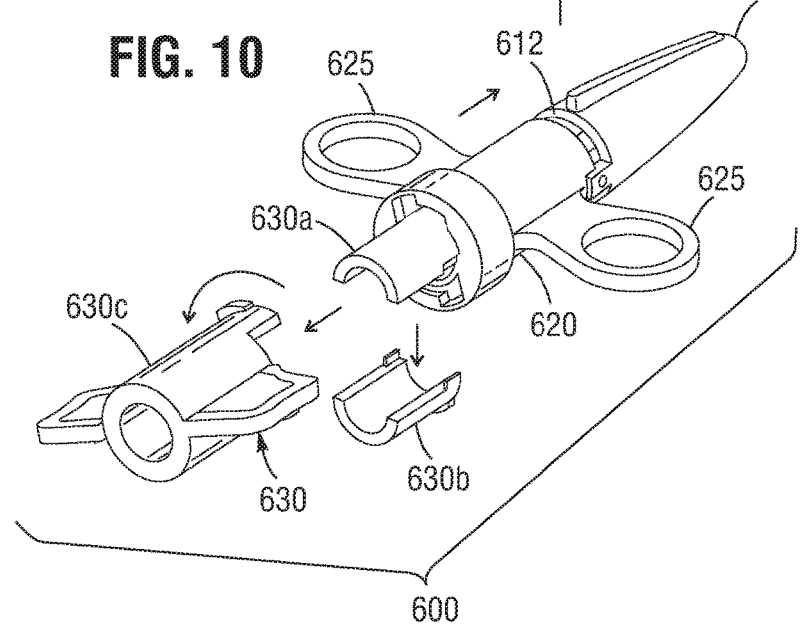
FIG. 10 is an exploded perspective view of the valve cover and the valve lock.

As shown in FIGS. 1-6, the entirety of the prosthetic valve 10 and its associated delivery system 400 can be secured and housed within a tray 100. The prosthetic valve 10 can be maintained in a compressed state around the distal portion 410 of the delivery system 400 by a valve cover 600 that is coupled to the prosthetic valve 10. As shown in FIGS. 9 and 10, a lock 300 can be secured to the valve cover 600 to protect the prosthetic valve 10 from damage resulting from movement along the delivery system 400. In one embodiment, the lock 300 can be positioned and configured to prevent the nose piece 412 from sliding into the prosthetic valve 10 and thus prevent the nose piece 412 from damaging the delicate leaflet tissue 14.

Returning to the features of the tray 100, the tray 100 can include a cavity 110 having an open end 112, a floor 114 and a peripheral side wall 120 defining a depth of the cavity 110.

Figure 1:
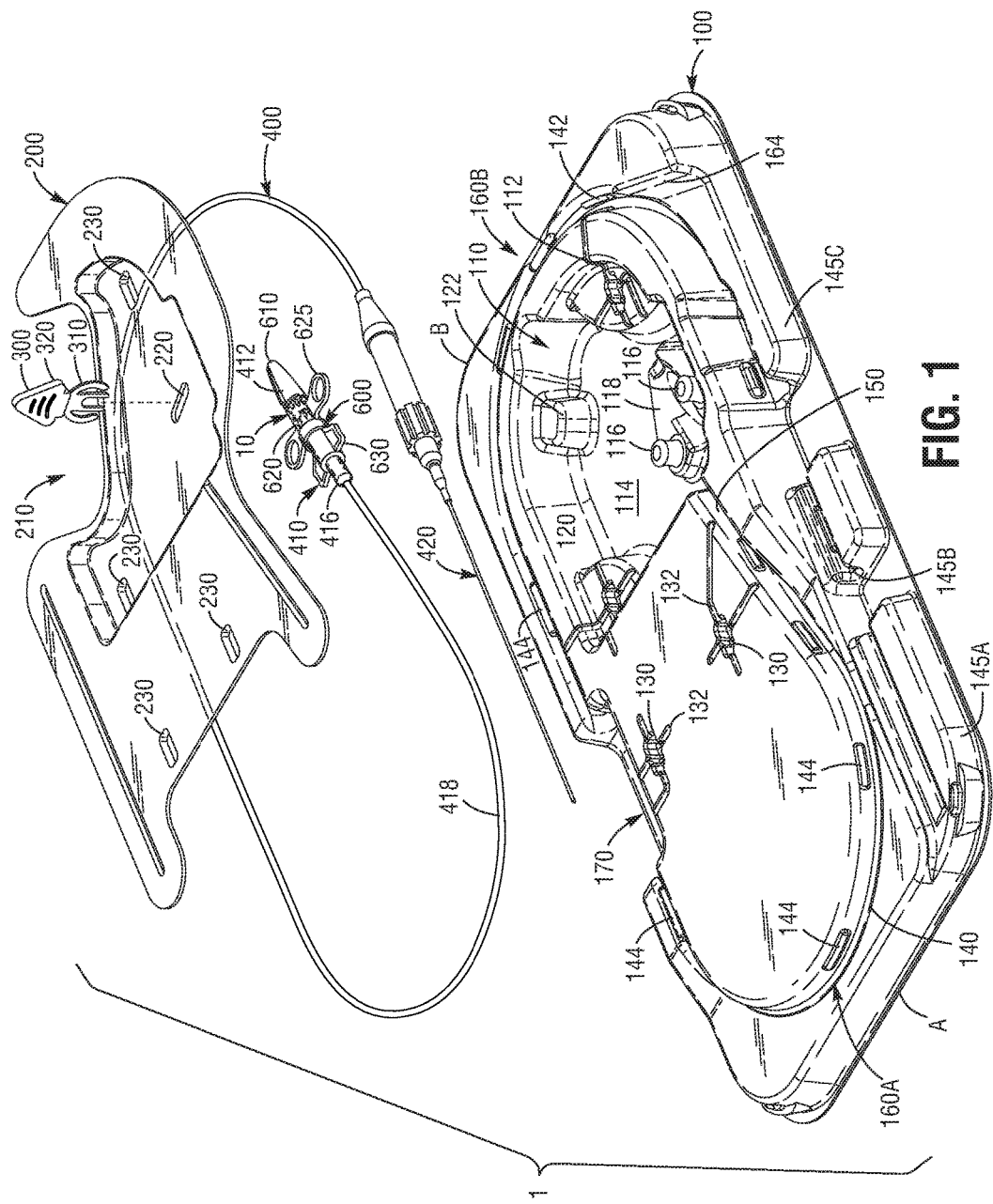
FIG. 1 is an exploded perspective view of an embodiment of a packaging system that includes a prosthetic valve and its associated delivery system for storage and transportation.
Figure 2:
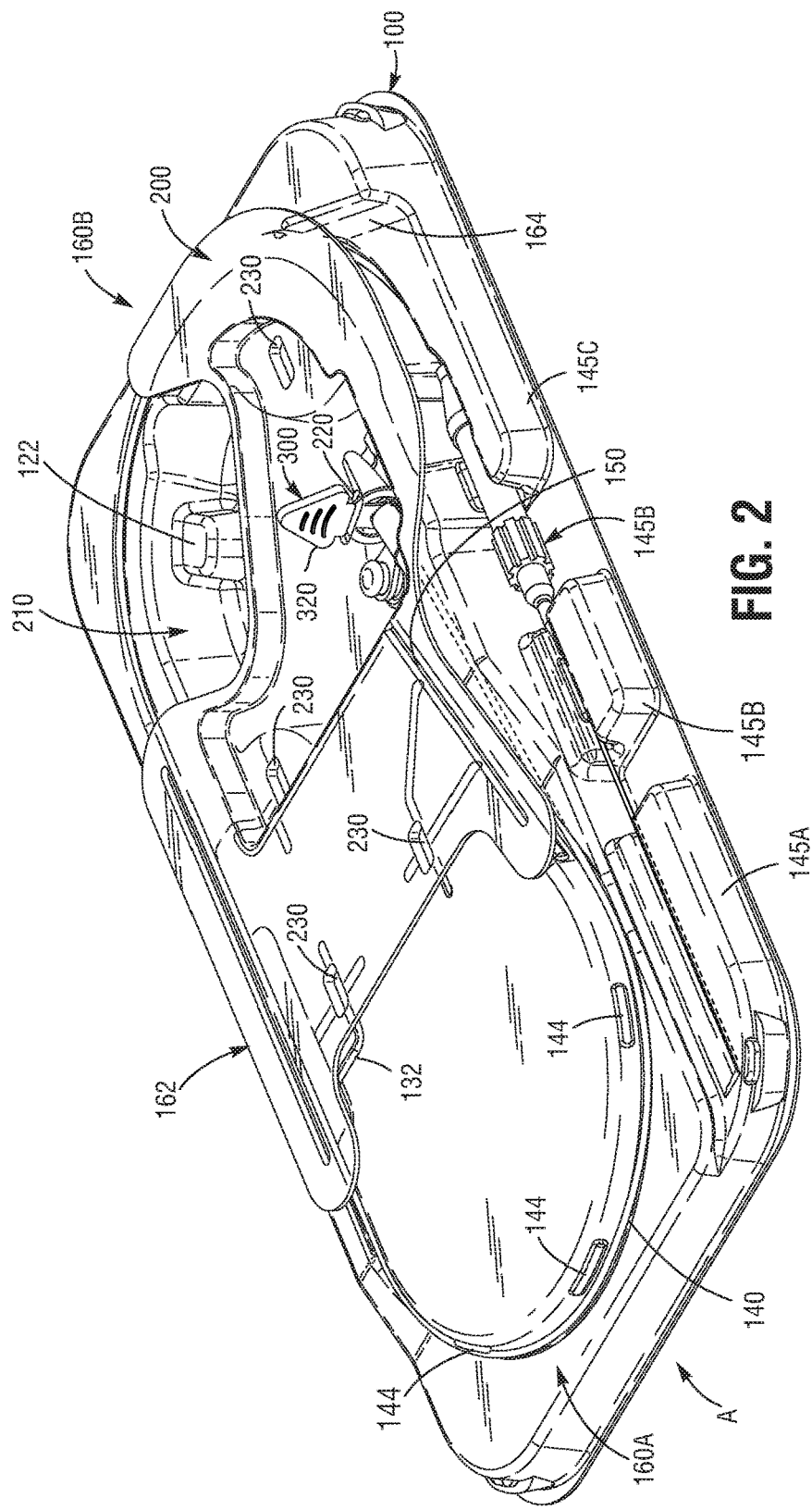
FIG. 2 is a perspective view of the assembled packaging system, prosthetic valve and associated delivery system of FIG. 1.
Figure 3:
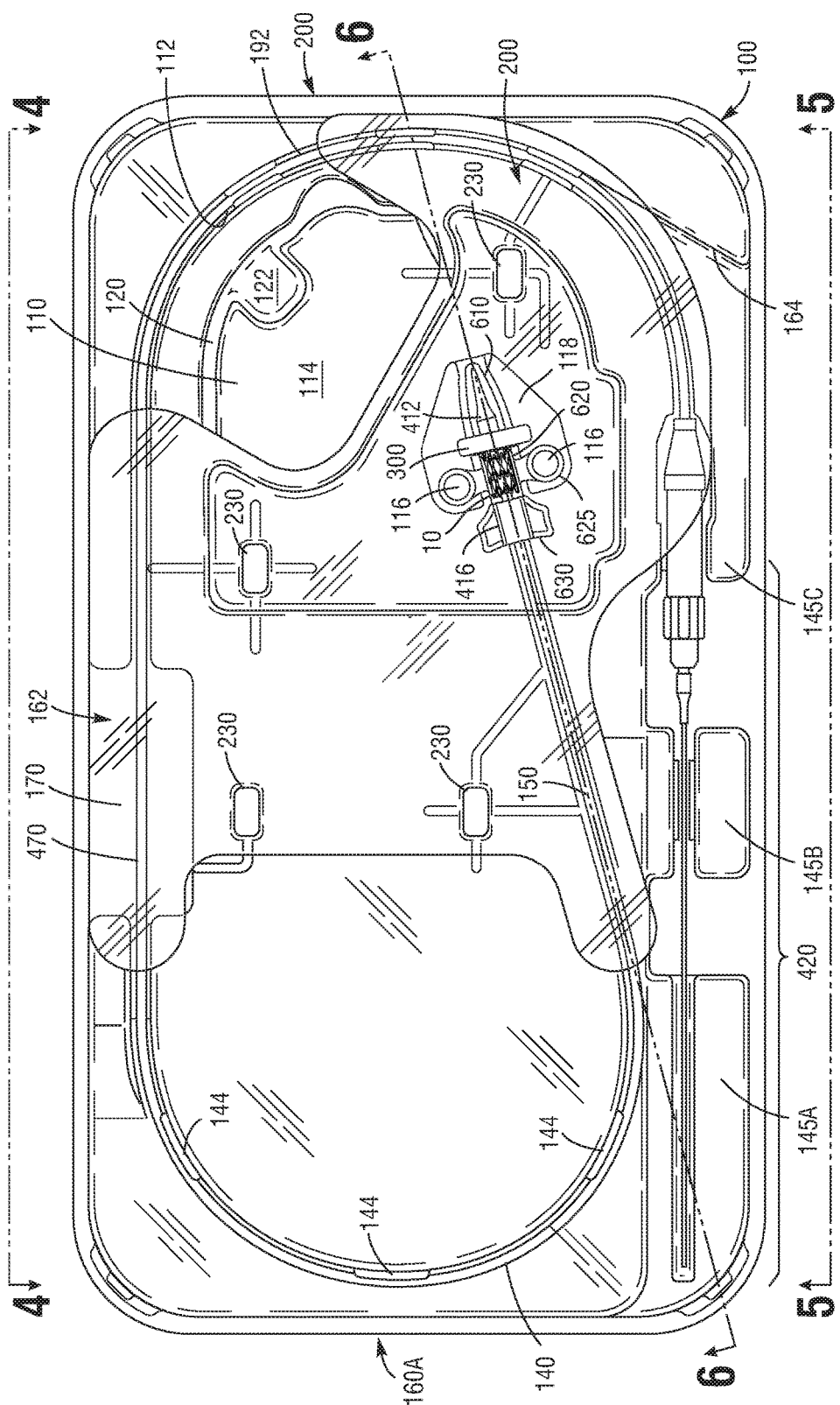
FIG. 3 is a top view of the packaging system, prosthetic valve and associated delivery system of FIG. 1.

The cavity 110 can be sized and shaped to house the prosthetic valve 10 and valve cover 600 coupled to the prosthetic valve 10. A lid 200 can be provided to partially enclose the open end 112 of the cavity 110. The lid 200 can be removably coupled to the tray 100 and can define an opening 210 to the cavity 110 when it is coupled to the tray 100, as shown in FIGS. 2 and 3. A first hydrating fluid can be poured into the cavity 110 through the opening 210 while the lid 200 is coupled to the tray 100. The cavity 110 can accommodate a volume of the first hydrating fluid that is sufficient to completely immerse the prosthetic valve 10, as indicated by a fill indicator or fill line 122 disposed from the peripheral side wall 120 between the floor 114 and the open end 112. The fill line 122 can also be disposed at a distance from the open end 112 in order to accommodate a volume of an additional second hydrating fluid that is used to flush the delivery system 400 while the prosthetic valve 10 is housed within the cavity 110. (See FIG. 11G). The first and second hydrating fluid can be the same or they may be different. In one embodiment, the first and second hydrating fluid is a saline solution.

In one embodiment, the prosthetic valve 10 can stored within the cavity 110 without a liquid preservative solution. The prosthetic valve 10 can stored in the absence of air (i.e., vacuum-sealed). The prosthetic valve 10 can also be stored in air, nitrogen gas, argon gas, or any other unreactive gas. It is understood that the biological tissue that comprises the flexible leaflet section 14 is subjected to treatment that permits it to be stored without a liquid preservative solution or to be stored in a substantially dry state. Similarly, it is understood that the entirety of the delivery system 400 can be stored in a similar manner as the prosthetic valve 10.

The lid 200 and the tray 100 are removably coupled together by a plurality of resilient mating pairs 130, 230. In the embodiment depicted in FIGS. 1-3, the lid 200 is depicted as comprising a plurality of protrusions 230 and the tray 100 is depicted as comprising a plurality of corresponding recesses 130. Gas flow channels 132 can be provided from the recesses 130 and a portion of the gas flow channels 132 can extend beyond the portion of the tray 100 that is covered by the lid 200 to ensure gas flow and sterilization of the packaging tray 100 and its contents when the lid 200 is coupled to the tray 100.

FIGS. 9 and 10 depict an embodiment of a valve cover 600 that can be used to house the prosthetic valve 10 and also to facilitate the loading of the prosthetic valve 10 within the delivery sheath 416. The valve cover 600 can include a nose cone 610 configured to house a nose piece 412, a central chamber 620 having a tapered internal cavity to house a prosthetic valve 10 in a first compressed state, and a fitted portion 630 to couple the valve cover 600 to the delivery system 400.

The tapered internal cavity of the central chamber 620 maintains at least a portion of the prosthetic valve 10 in a first compressed state having a diameter that is smaller than a diameter of the heart valve 10 when it is deployed from the delivery system 400 and implanted in a patient (FIG. 7). The internal cavity can have a tapered surface having a diameter that is progressively narrowed toward the delivery sheath 416. The tapered surface can help guide and fully crimp the prosthetic valve 10 as it is loaded into the delivery sheath 416 into a second diameter within the delivery sheath 416 that is smaller than the first diameter within the internal cavity of the delivery sheath 416.

The fitted portion 630 is depicted as comprising three interlocking pieces 630a, 630b, 630c, in which interlocking pieces 630a and 630b are mated together to provide frictional engagement with the delivery sheath 416 and is held together by sliding 630c over interlocking mating pair 630a, 630b and twisting 630c in a locked position. It is understood that the frictional engagement of the fitted portion 630 is not so tight as to prevent the delivery sheath 416 from slidably moving axially or distally relative to the fitted portion 630.

The valve cover 600 can further comprise wings 625 extending laterally from opposing sides of the valve cover 600 to couple the mounting surface 116 in the cavity 110 of the tray 100. The wings 625 can comprise apertures shaped to resiliently engage mounting surface 116 to stabilize and prevent the valve cover 600 from moving or rotating during storage, transportation and loading the prosthetic valve 10 within the delivery sheath 416.

In the embodiment depicted in FIGS. 1-6, the mounting surface 116 is depicted as a pair of thermoformed protrusions formed from the cavity floor 114 that are shaped to resiliently engage corresponding recesses or openings formed in the wings 625. The cavity floor 114 may further include a shaped recess 118 to conform to the outer contours of the valve cover 600 that is facing the floor 114 so as to further stabilize the valve cover 600 from moving or rotating. Although the mounting surface 116 is depicted as protrusions, it is understood that the mounting surface 116 can be one of a pair of protrusions or a pair of recesses or openings that are configured to mate with corresponding features of the wings 625. The corresponding features of the wings 625 can be the other of the pair of protrusions or the pair of recesses or openings. Preferably, the wings 625 and mounting surface 116 are in resilient snap-fit engagement.

A lock 300 can optionally be provided to engage with the valve cover 600. As further depicted in FIGS. 9 and 10, the lock 300 can be coupled to the valve cover 600. In one embodiment, the lock 300 can comprise a first end 310 and a second end 320.

The first end 310 of the lock 300 can comprise a first pair of prongs 312 configured to be inserted into an opening 612 between the nose cone 610 and the central chamber 620 and a second pair of prongs 314 configured to fit externally around the valve cover 600. The first pair of prongs 312 prevents the nose piece 412 from sliding into the prosthetic valve 10 and thus functions to maintain the nose piece 412 substantially within the nose cone 610. The first pair of prongs 312 can also be positioned to maintain a separation between the nose piece 412 and the prosthetic valve 10. Stabilizing the nose piece 412 relative to the prosthetic valve 10 prevents the nose piece 412 from sliding into and damaging the fragile leaflets 14 of the prosthetic valve 10. In one embodiment, the first pair of prongs 312 can be provided between the second pair of prongs 314. The second pair of prongs 314 is resiliently secured externally of the valve cover 600.

The second end 320 of the lock 300 can be configured to protrude externally of the cavity 110 and through an aperture 220 disposed on the lid 200, as shown in FIG. 2. The second end 320 can be sized and/or shaped to prevent it from passing through the aperture 220, such as by providing a second end 320 that is larger than the aperture 220. Alternatively, the second end 320 can be fixed to or integrated with the lid 200. Regardless, the second end 320 is configured to cooperate with the lid 200 such that removing the lid 200 will also remove the first end 310 of the lock 300 from the valve cover 600 and the elongated delivery system 400.

Returning to the features of the tray 100 in FIGS. 1-6 an engaging surface 140 can be provided externally or peripherally of the cavity 110. At least a portion of the engaging surface 140 can be elevated above the cavity floor 114 and a ramp 150 can be provided to extend between the engaging surface 140 and the cavity 110. In one embodiment, the ramp 150 extends downwardly from the engaging surface 140 and into the cavity 110 through an opening 152 defined in the peripheral side wall 120 and adjacent the cavity floor 114. In another embodiment, the ramp 150 extends downwardly from the engaging surface 140 to the floor of the cavity 110. As illustrated in FIG. 6, the angle θ of the ramp 150 may be from about 4 degrees to about 10 degrees relative to a horizontal plane bisecting the tray 100. The angle θ of the ramp 150 is selected so as to prevent any fluid contained in the cavity 110 from leaking out of the tray 100.

The engaging surface 140 and the ramp 150 are configured to secure at least a portion of the delivery system 400 externally of the cavity 110. One or both of the engaging surface 140 and the ramp 150 can comprise a channel 142 formed in the tray 100 and shaped to accommodate a portion of the delivery system 400, such as a the main catheter 418, along a portion of its length or along the entirety of its length extending externally of the cavity 110. The engaging surface 140 can also comprise a plurality of tabs 144 configured to resiliently engage parts of the delivery system 400 or main catheter 418 within the channel or to the tray 100.

As shown in FIG. 2, the engaging surface 140 can include curved sections 160A, 160B on opposing sides of the tray 100 and at least one straight section 162 to maintain the elongated delivery system 400 and thus to provide a more compact storage. The delivery system 400 can be positioned and maintained in that configuration by the plurality of tabs 144.

As shown in FIG. 4, the straight section 162 can comprise a space 170 in which the delivery system 400 is not in direct contact with the tray 100. The space 170 is provided around a free segment 470 of the elongated delivery system 400 externally of the cavity 110 to permit a user's hand to grasp the free segment 470 and lift at least a portion of the elongated delivery system 400 on both sides of the free segment 470 out of engagement with the tray 100 and without causing disengagement of the remaining portions of the delivery system 400 from the tray 100.

As shown in FIG. 5, the proximal portion 420 of the delivery system 400 is engaged within a periphery of the tray 100 in formed recesses 145A, 145B and 145C shaped to accommodate the external contours of the proximal portion 420. A support surface 164 can be provided to maintain the proximal portion 420 of the delivery system 400 in position for coupling with a handle 80 when the proximal portion 420 is disengaged from and extends away from the tray 100, as shown in FIG. 11E.

In one embodiment, the packaging system 1 comprising the prosthetic valve 10 and its associated delivery system 400, which are both maintained with the tray 100, is packaged within a sterile pouch 70 (FIG. 11C) and then sterilized by gas, such as by ethylene oxide or by gamma irradiation or electron beam irradiation. In one embodiment, the sterile pouch 70 is gas impermeable and can comprise Tyvek materials from DuPont. After the sterilization, the sterile pouch 70 is then placed within a second pouch 60 (FIG. 11B). The second pouch 60 can be moisture impermeable, gas impermeable or both (e.g., a foil pouch). The second pouch 60 containing the sterile pouch 70 and the packaging system 1 may then be provided in a box 50 for shipment (FIG. 11A).

Figure 11A:
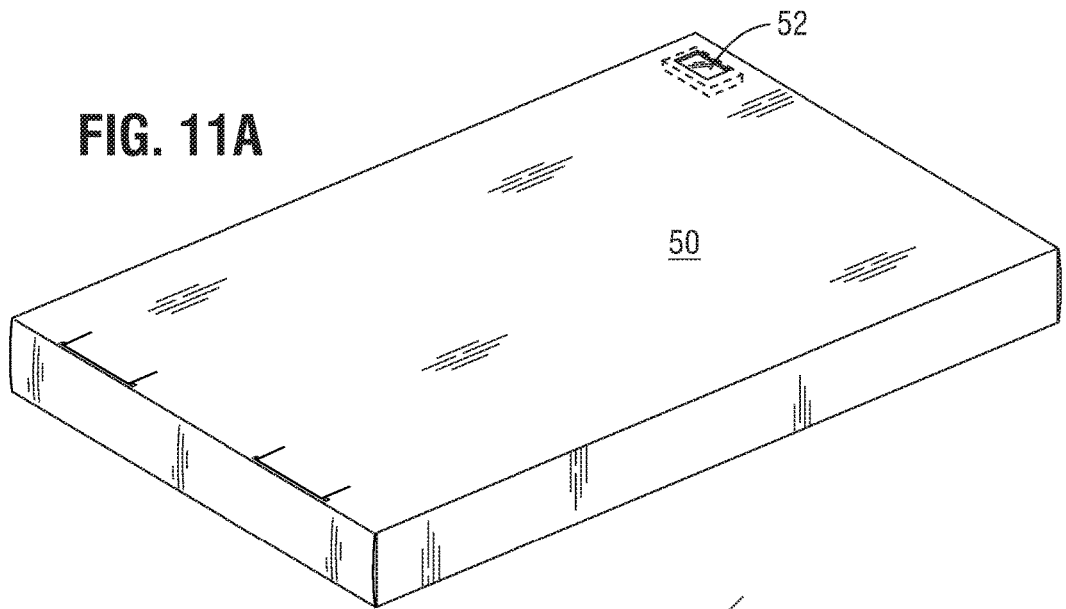
FIGS. 11A through 11I depict the sequence of steps that are performed in preparing a heart valve and its associated delivery device for implantation using an exemplary embodiment of the packaging system.
Figure 11B:
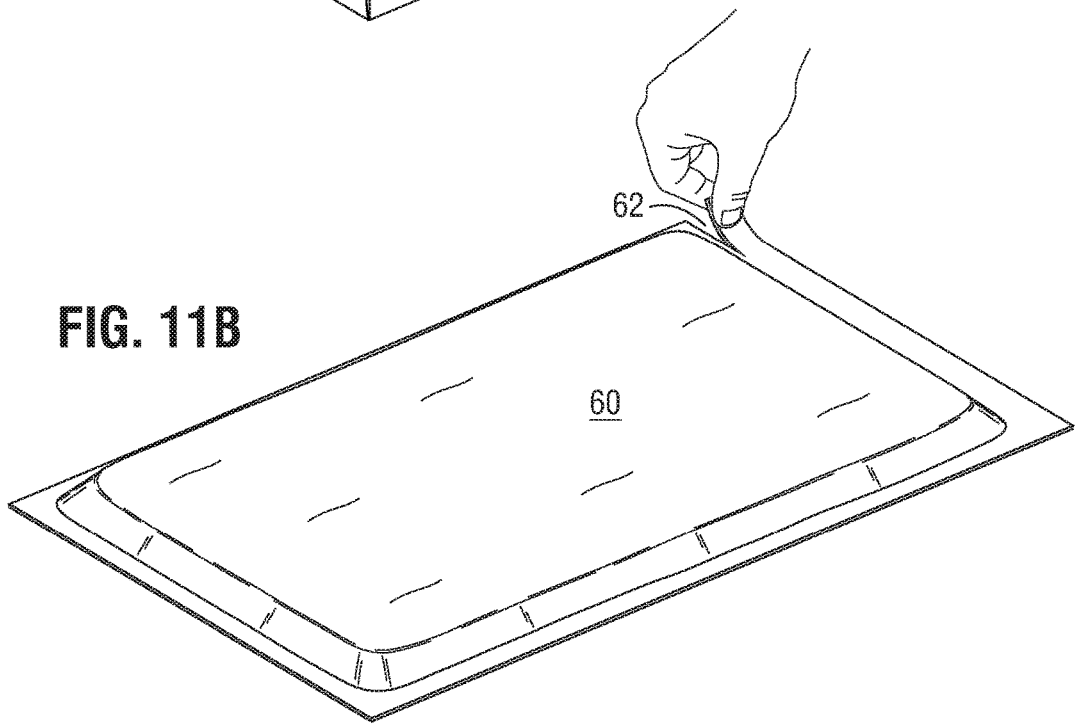
Figure 11E:
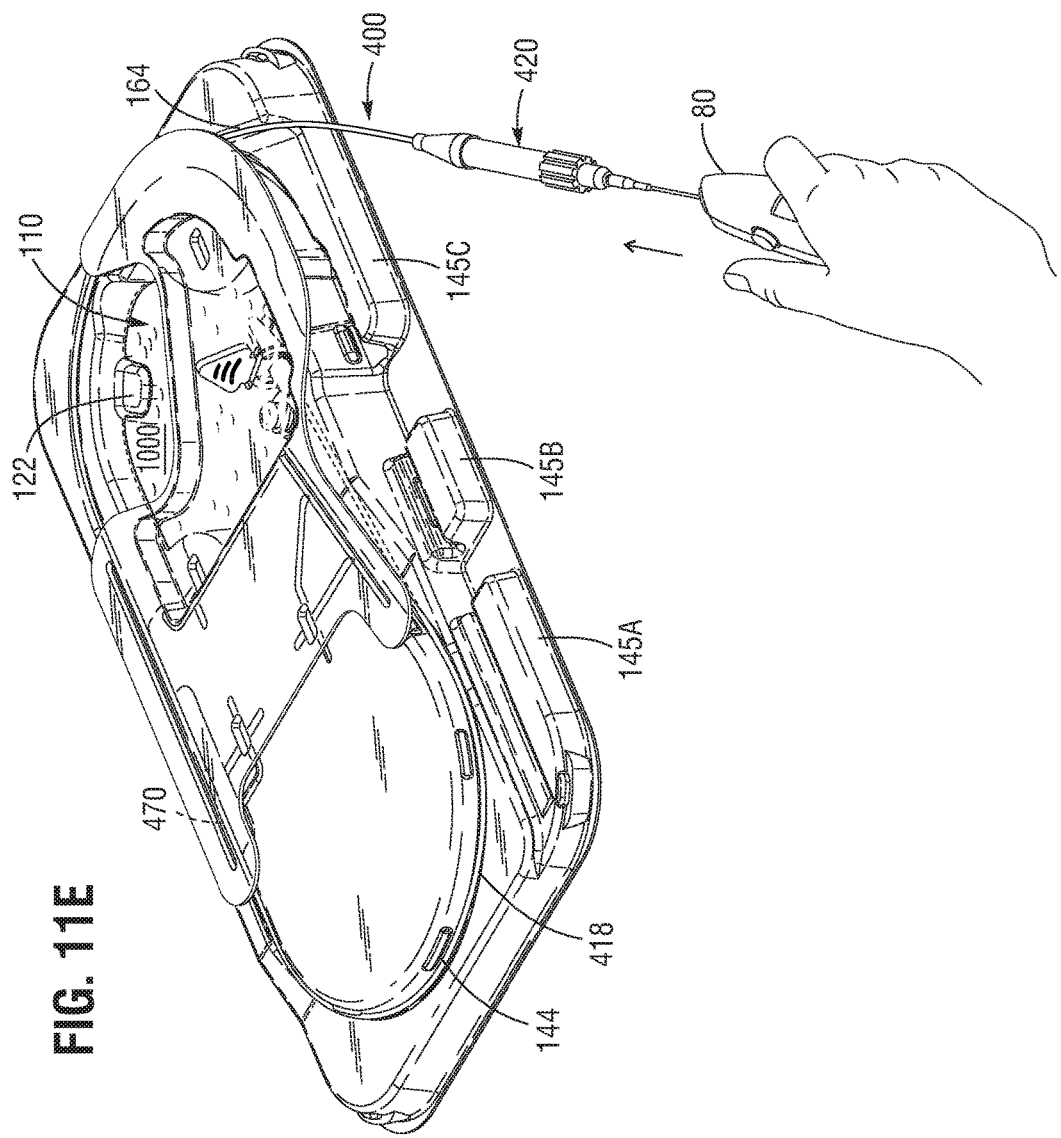

FIGS. 11A-11I depict the exemplary steps for preparing and assembling the prosthetic valve 10 and the delivery system 400 using the packaging system 1. FIGS. 11A-11C depict sequence of removing the packaging tray 100 from its outer packaging.

In a first step illustrated in FIG. 11A, once the box 50 is received, reference is made to a temperature sensor 52 to ascertain whether the box 50 has been subjected to unacceptable temperature excursions. In one embodiment, the temperature sensor 52 will indicate if the box 50 has been subjected to a temperature excursion outside of the range of from about −18° C. to about 45° C. If the box 50 has been subjected to a temperature outside of the acceptable range, then the prosthetic valve 10 and the delivery system 400 cannot be used for implantation of the heart valve 10 in a patient.

If the box 50, however, has not been subjected to unacceptable temperature excursions outside of the acceptable range, then the foil pouch 60 is removed from the box 50. FIG. 11B depicts the foil pouch 60 being opened along a tear line 62. The foil pouch 60 is gas impermeable and is provided to protect the packaging system 1 from moisture. Once the foil pouch 60 is torn open along the tear line 62, another pouch 70 containing the packaging system 1 is removed. It is understood that the handling of the box 50, foil pouch 60 and the pouch 70 can take place in a non-sterile field of the operating room.

The step in FIG. 11C illustrates the transfer of the packaging system 1 from the non-sterile field to the sterile field and requires one person in the non-sterile field to open and handle the pouch 70 and another person in the sterile field to handle the packaging system 1 and transfer it into the sterile field. In one embodiment, the step in FIG. 11C can be performed by a single person by simply opening the pouch 70 and sliding the packaging system 1 from a nonsterile field to a sterile field. In one aspect of this embodiment, the person opening the pouch 70 is in the non-sterile field and avoids any direct physical contact with the packaging system 1 as it is slid or otherwise transferred onto, for example, a table in the sterile field. In another embodiment, the step in FIG. 11C can be performed by two people, in which one person handles and opens the pouch 70 in the non-sterile field and another person receives and removes the packaging system 1 from the pouch 70 in the sterile field. In accordance with one aspect of this embodiment, the cavity does not comprise a liquid or a preservative solution.

The steps exemplified by FIGS. 11D through 11I are understood to be performed in the sterile field of the operating room.

In FIG. 11D, a first hydrating fluid 1000 is poured into the cavity 110 up to the fill line 122 so as to completely immerse the prosthetic valve 10. While the heart valve 10 is hydrating, the handle 80 can be prepared and attached to the proximal portion 420 of the delivery system 400.

In FIG. 11E, the proximal portion 420 of the delivery system 400 is removed from secured engagement with the tray 145A, 145B, 145C and is permitted to resiliently extend beyond the periphery of the tray 100, supported by the support surface 164 for engagement with the handle 80.

Figure 11F:
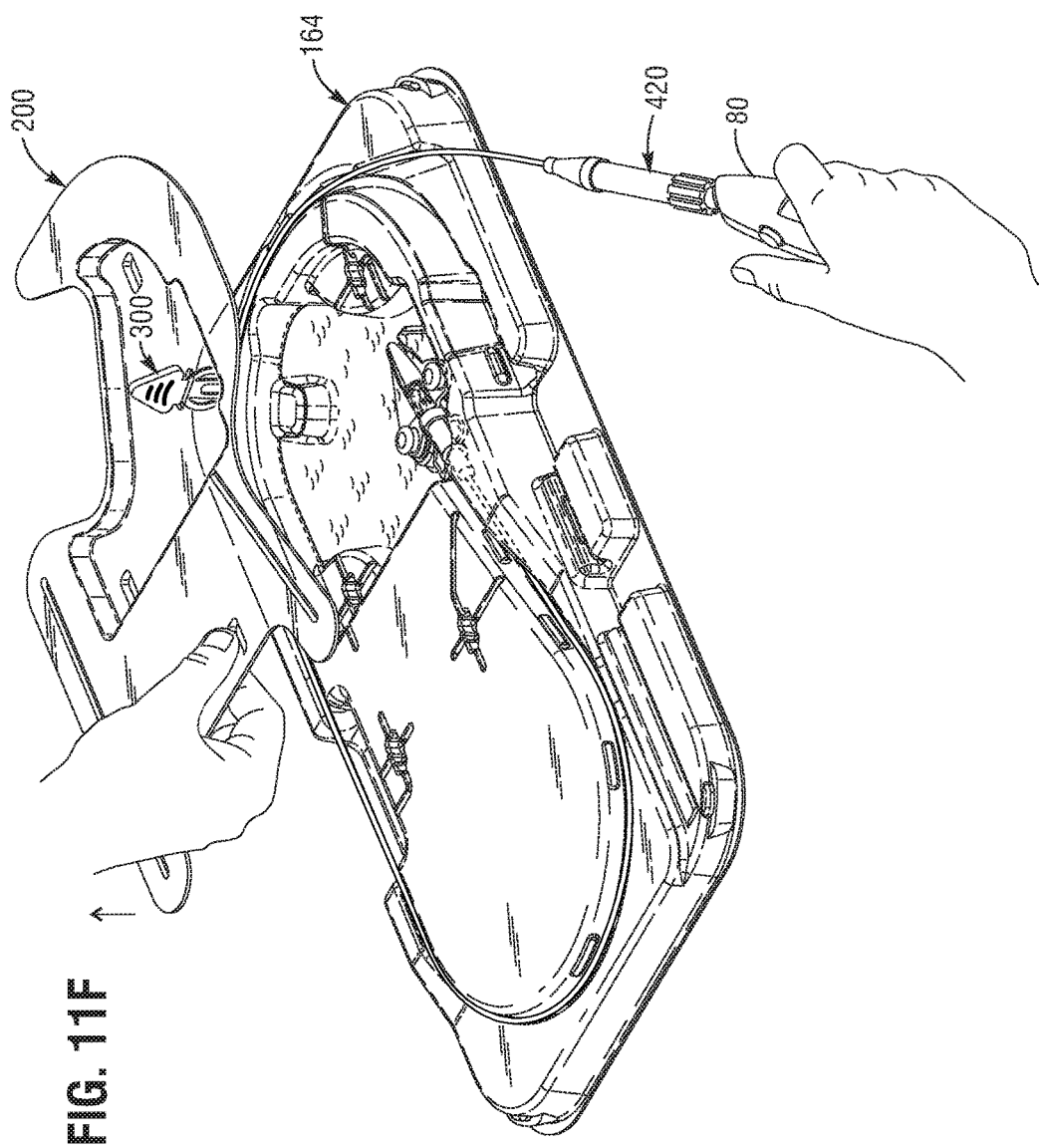

In FIG. 11F, the lid 200 can be removed from the tray 100 and removal of the lid 200 can also remove the lock 300 from the valve cover 600. The integration of the lock 300 with the cover 600 ensures that the lock 300 is removed prior to loading the heart valve 10 within the delivery sheath 416, as failure to remove the lock 300 prior to loading would likely result in damage to the leaflet structure of the heart valve 10.

A flushing step can be performed to remove any air bubbles C from within the delivery system 400. In FIG. 11G, a second hydrating fluid 2000 is injected into the handle 80, which passes through the proximal portion 420, through a lumen extending through the delivery system 400, and out of the distal portion 410. The injection of the second hydrating fluid 2000 through the delivery system 400 can be performed to flush out any air bubbles C that can be present within the delivery system 400 and can be determined to be completed when air bubbles C are no longer liberated from the distal portion 410 of the delivery system 400.

Figure 11H:
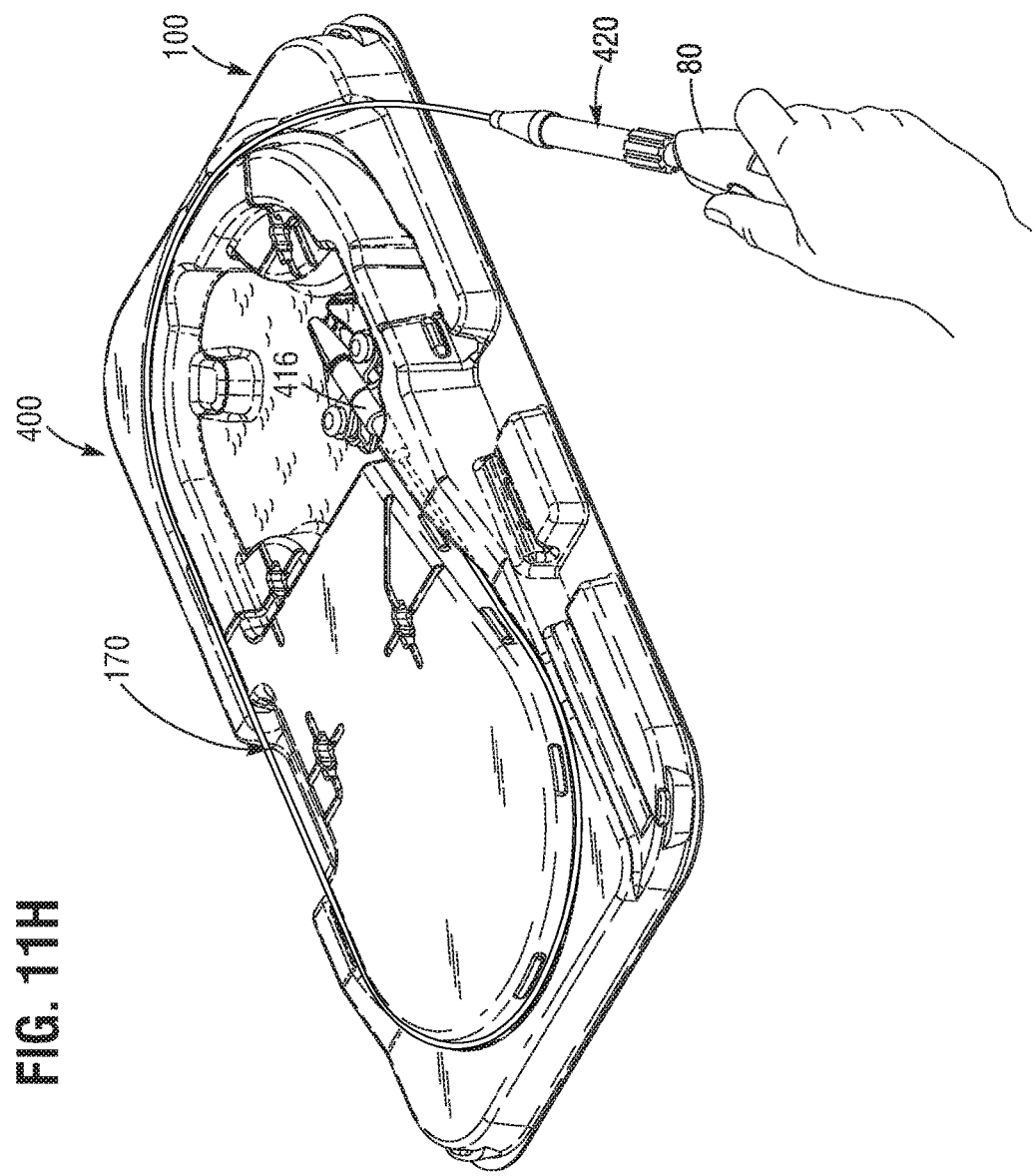
Figure 11:
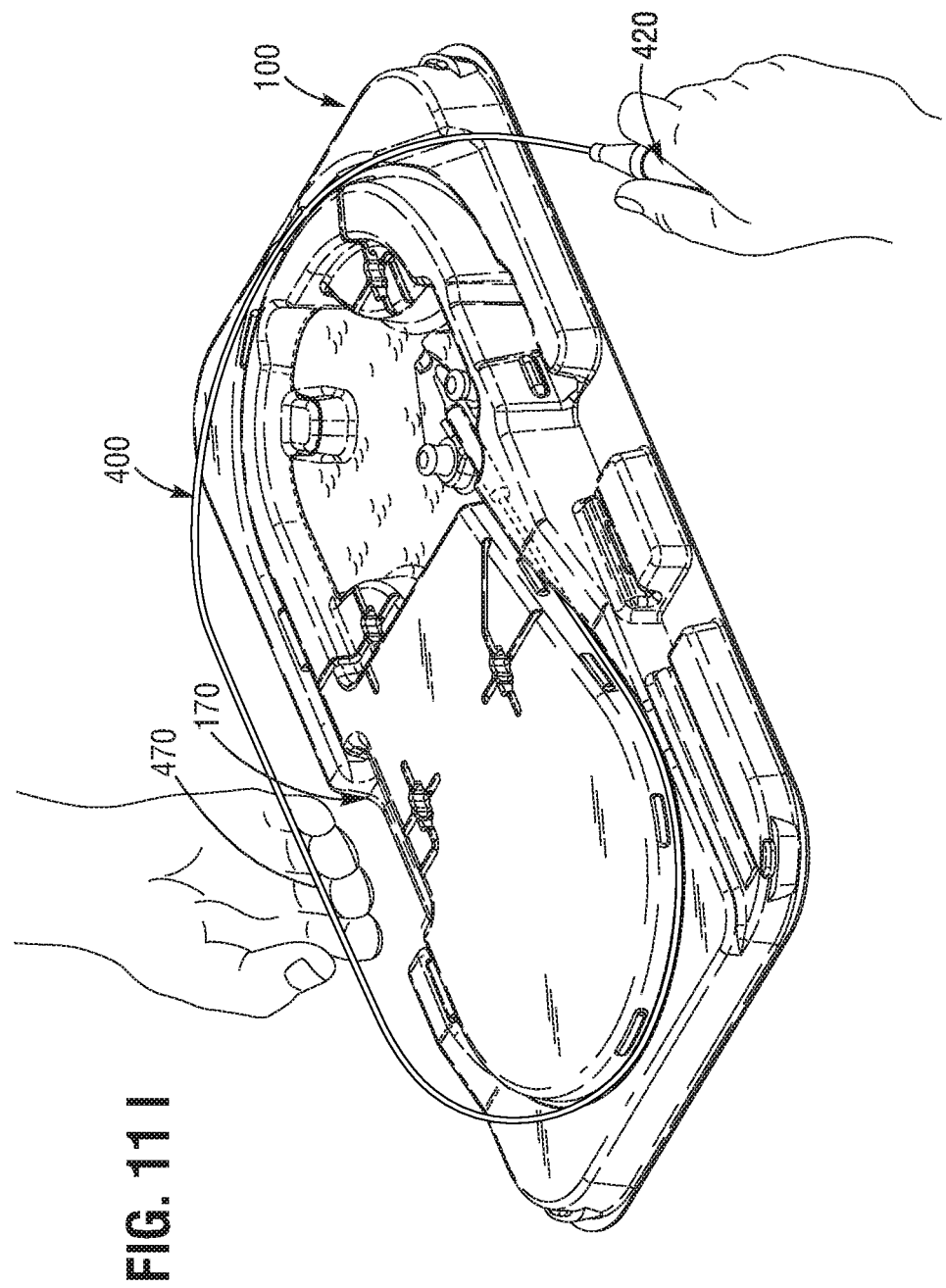

The heart valve 10 can be loaded within the delivery sheath 416 after the flushing is completed. FIG. 11H depicts the prosthetic valve 10 being loaded within the delivery sheath 416. The loading of the heart valve 10 within the delivery sheath 416 can accomplished by the handle 80 causing the actuation of the delivery sheath 416 over the heart valve and towards the nose piece 412. The actuation of the delivery sheath 416 may involve both axial movement in a distal direction as well as rotational movement, which generates substantial torque forces. FIGS. 8A and 8B depict the actuation of the delivery sheath 416 from an unloaded configuration (FIG. 8A) to a loaded configuration in which the heart valve 10 is contained within the delivery sheath 416 (FIG. 8B). The prosthetic valve 10 can loaded within the delivery sheath while the valve cover 600 is attached to the delivery system 400 and the wings 625 are resiliently engaged with the mounting surface 116. This permits stabilization of the heart valve 10 and its associated delivery system 400 from the torque forces which are exerted as the delivery sheath 416 is advanced distally over the heart valve 10.

The wings 625 of the valve cover 600 can be configured to extend laterally from opposing sides of the valve cover 600 to couple the mounting surface 116 disposed from the cavity floor 114. The wings 625 can comprise apertures shaped to resiliently engage mounting surface 116 which are provided on the tray 100 to stabilize and to prevent the valve cover 600 from moving or rotating during storage, transportation and loading the prosthetic valve 10 within the delivery sheath 416. In addition, the cavity floor 114 may further include a shaped recess 118 to conform to the outer contours of the valve cover 600 that is facing the floor 114 so as to further stabilize the valve cover 600 from moving or rotating.

Once the prosthetic valve 10 is loaded within the delivery sheath 416, the valve cover 600 can be removed from the distal portion 410 of the delivery system 400 by first twisting and removing interlocking piece 630c to permit disassembly of interlocking pieces 630a and 630b. See FIG. 10. This will permit the distal portion 410 of the delivery system 400 to slide out of the remaining portion of the valve cover 600.

FIG. 11I depicts the removal of the delivery system 400 with the prosthetic valve 10 loaded within the delivery sheath 416 and the valve lock 600 removed from the distal portion 410. The delivery system 400 can be removed from the tray 100 by grasping a free segment 470 in a space 170 of the tray 100 and removing the delivery system 400 from engagement with the tray 100. The free segment 470 of the delivery system 400 can be a portion of the delivery system 400 that is not in direct contact with the tray 100. The space 170 may have a width that permits a hand grip around the free segment 470 to pull at least a portion of the delivery system 400 out of engagement with the tray 100. The other hand can, but is not required, to support the proximal end 420 of the delivery system 400.

FIGS. 12-19 depict another embodiment of the packaging system 1000 that can be used to store, transport and prepare a replacement heart valve together with its associated delivery system 1200 for use in the operating room. The replacement heart valve (not shown) can be the same as the heart valve 10 described above with reference to FIG. 7. Similarly, the delivery system 1200 that can be packaged in the packaging system 1000 can be the same as the delivery system 400 described above with reference to FIGS. 8A and 8B. The differences between the packaging system 1000 described with reference to FIGS. 12-19 reside in the structure of the tray 1100, the valve cover 1210 that houses the replacement heart valve and a portion of the distal end of the delivery system 1200. As more fully described below, these differences change the certain aspects of the steps in preparing and assembling the replacement heart valve as described above in reference to FIGS. 11A-11I.

As shown in FIGS. 12, 13, 14A, 14B and 19, the tray 1100 can store and transport the delivery system 1200, including a prosthetic valve (not shown) that is housed within a valve cover 1210. The valve cover 1210 is removably associated with the delivery system 1200 while it remains affixed to the tray 1100. The tray 1100 is also configured to store and transport the handle 1230 associated with the delivery system 1200. In the embodiment depicted in FIGS. 12, 13, 14A and 14B, the handle 1230 can be stored within the tray 1100 attached to the delivery system 1200. In another embodiment (not depicted), the handle 1230 can be stored within the tray 1100 detached from the delivery system 1200.

The tray 1100 can be made of any material that can be formed to securely and removably attach at least the valve cover 1210 and the handle 1230 from movement during storage and transportation. The tray 1100 is dimensioned such that the catheter portion 1220 of the delivery system 1200 can be arranged or affixed to the tray 1100 with a single curve or U-shaped turn so as to reduce the torque required during the loading operation of the delivery system 1200 in which the valve is loaded inside the delivery sheath prior to implantation. The catheter portion 1220 between the valve cover 1210 and the handle 1230 can be fixed within the tray by one or more resilient tabs 1128 to provide a snap-fitting engagement of the catheter portion 1220 within a groove or recess disposed within the tray 1100. FIG. 14B depicts a pair of resilient tabs 1128 disposed on only one side of the tray 1100.

The tray 1100 includes a cavity 1130 that is formed to house the valve cover 1210. The valve cover 1210 houses the prosthetic valve, which is mounted on the distal portion of the delivery system 1200. As described above, the prosthetic valve can be partially contained within the delivery sheath on one end and is adjacent a nose cone on the other end. The floor of the cavity 1130 can comprise a mounting surface 1112 that is formed to resiliently engage at least a portion of the external surface of valve cover 1210 so as to prevent movement of the valve cover 1210 during storage, transportation, preparation and loading of the prosthetic valve within the delivery sheath. The mounting surface 1112 can comprise a surface contoured to substantially conform with a portion of the external surface of the valve cover 1210 and thus provide an engaging and resilient fit that prevents movement of the valve cover 1210 within the cavity 1130.

Figure 12:
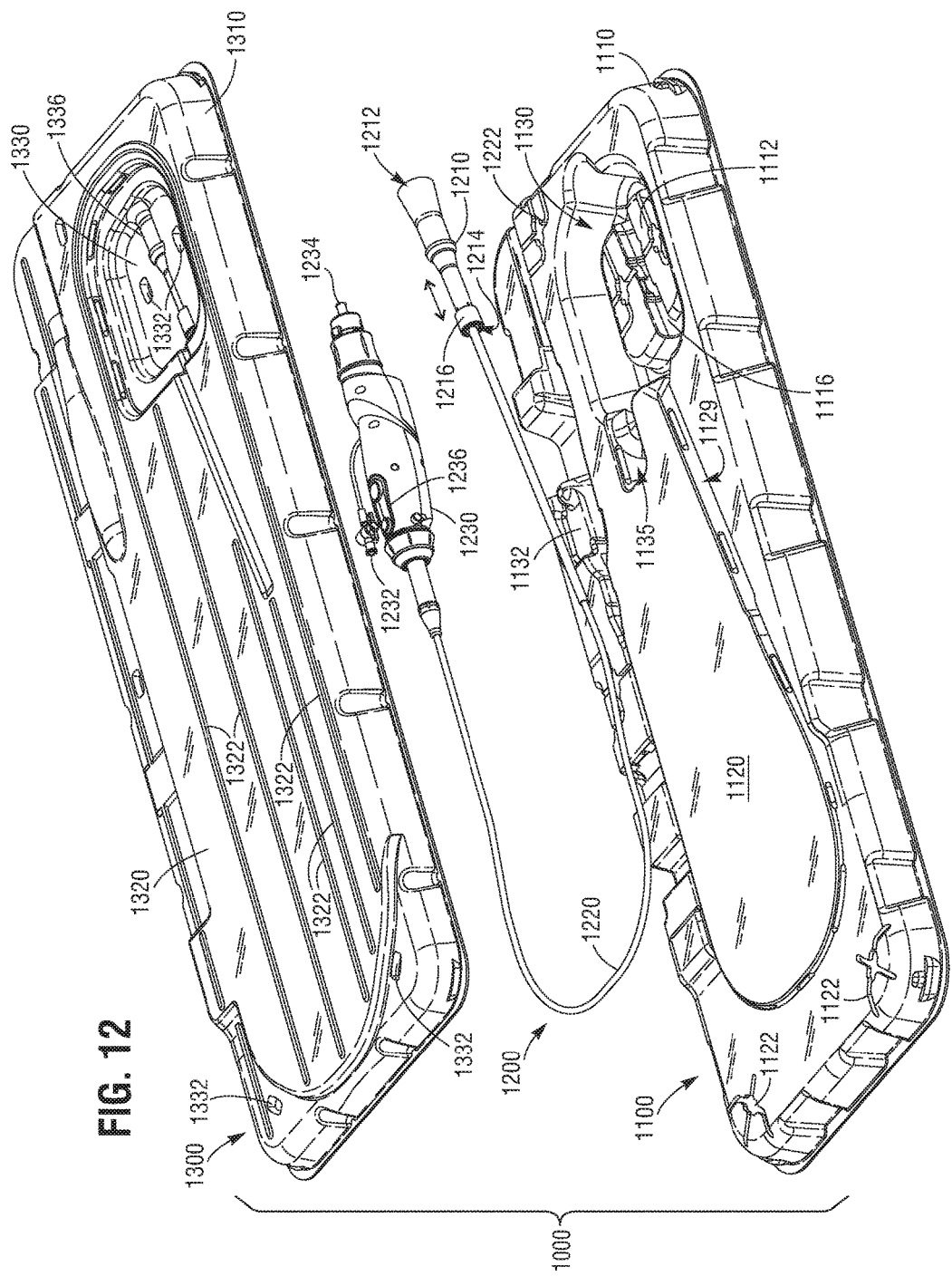
FIG. 12 is an exploded perspective view of another embodiment of a packaging system comprising, from bottom to top, a tray, a prosthetic valve delivery system, and a lid.
Figure 14A:
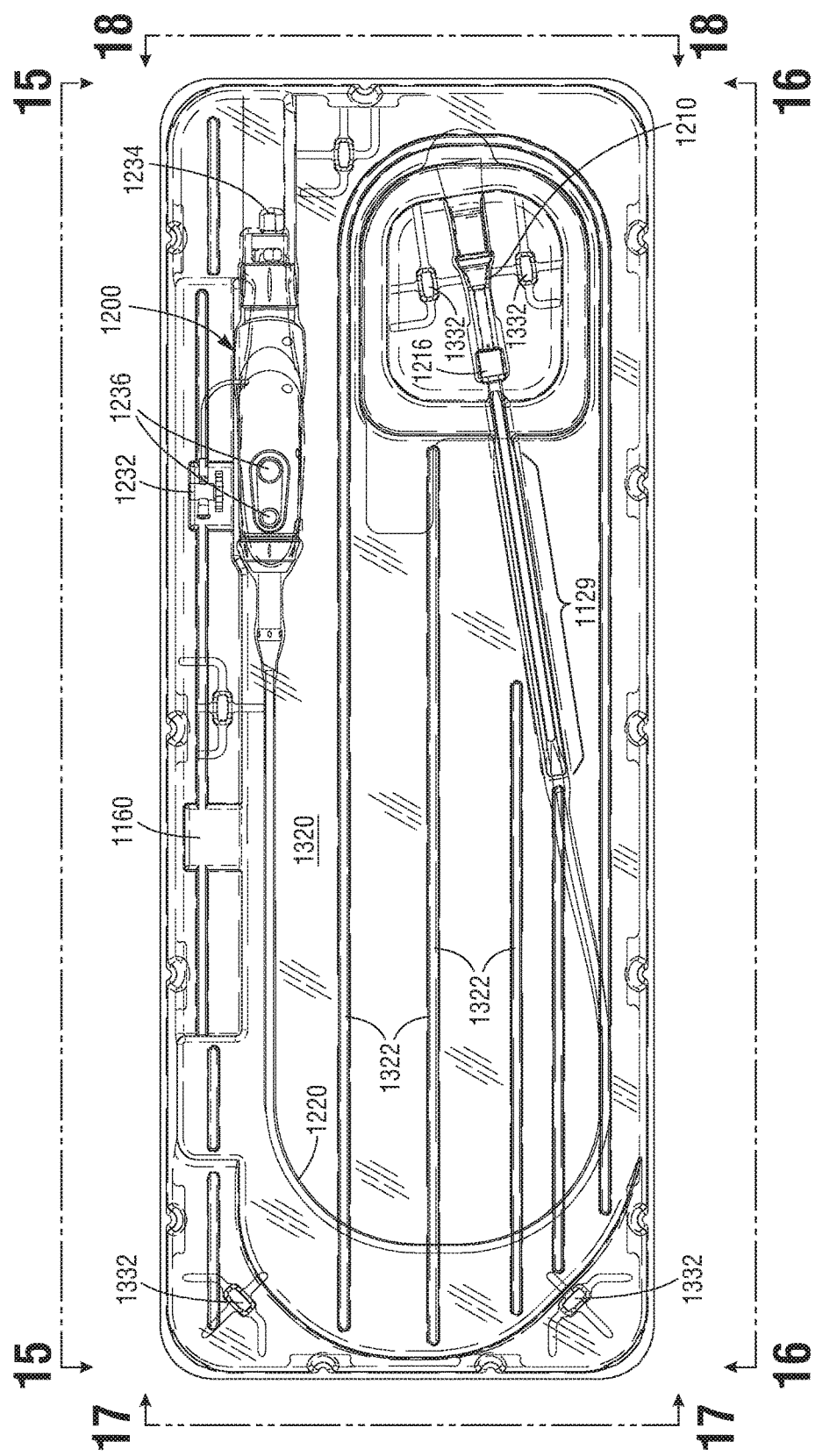
FIG. 14A is a top view of the assembled packaging system of FIG. 13.
Figure 14B:
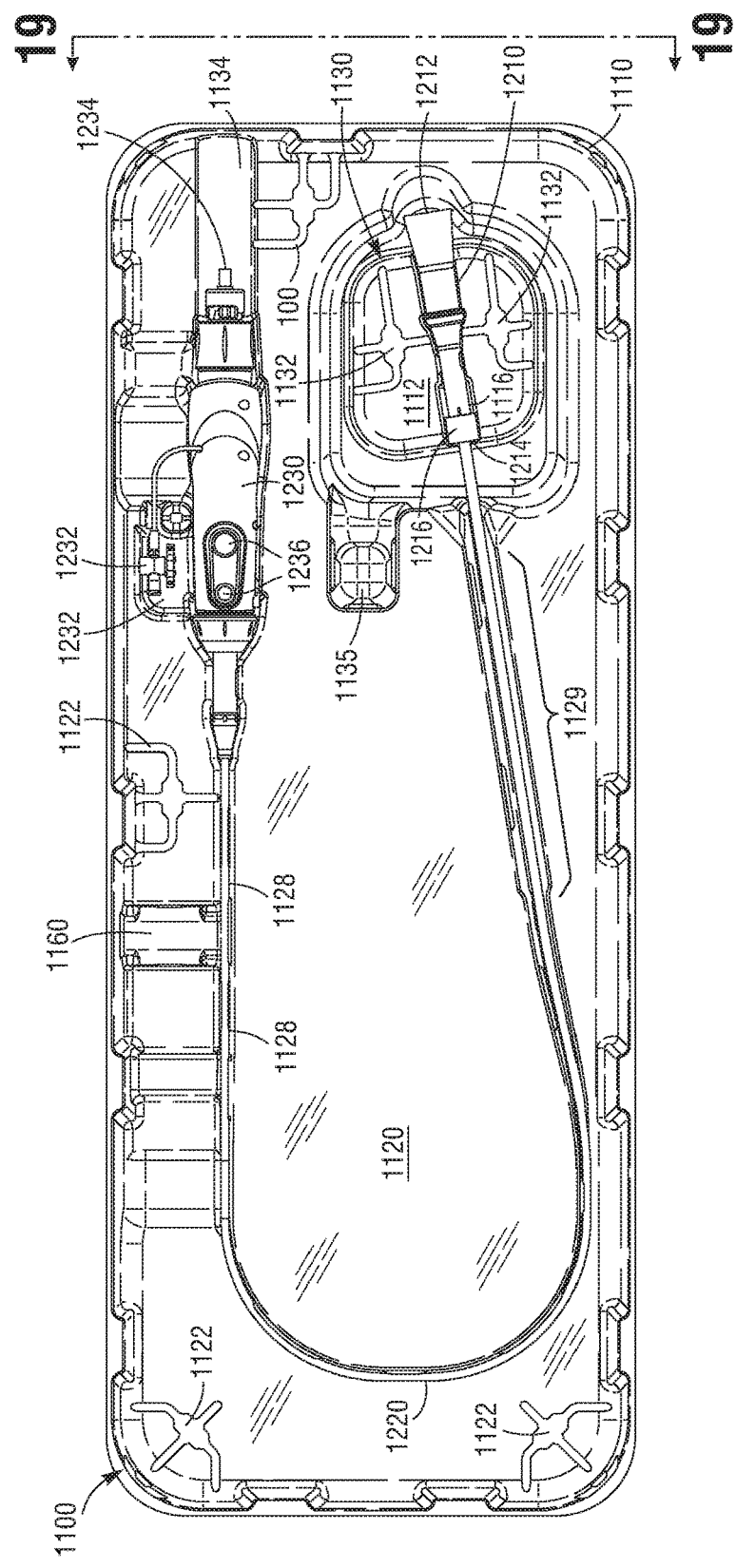
FIG. 14B is a top view of the packaging system of the assembled packaging system of FIG. 13 without the lid.
Figure 15:
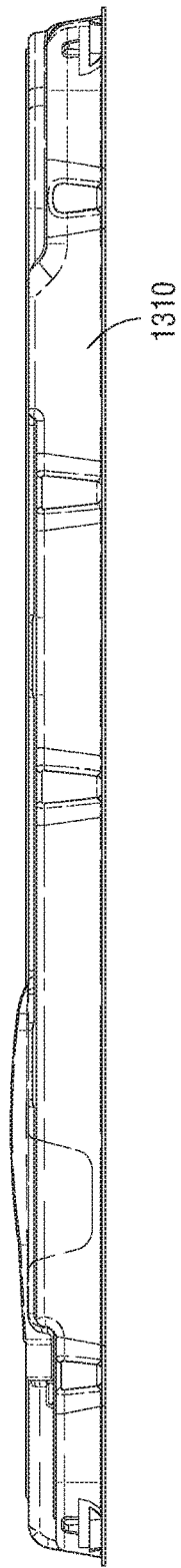
FIG. 15 is an elevation view of side 15-15 of the assembled packaging system of FIG. 14A.
Figure 16:
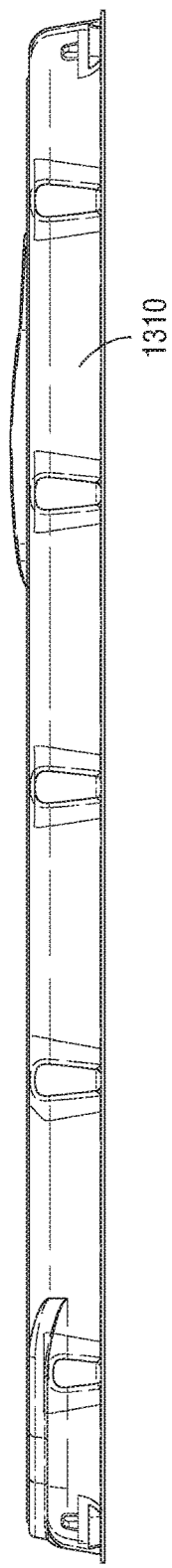
FIG. 16 is an elevation view of side 16-16 of the assembled packaging system of FIG. 14A.
Figure 17:
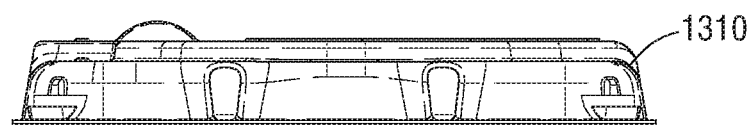
FIG. 17 is an elevation view of side 17-17 of the assembled packaging system of FIG. 14A.
Figure 18:
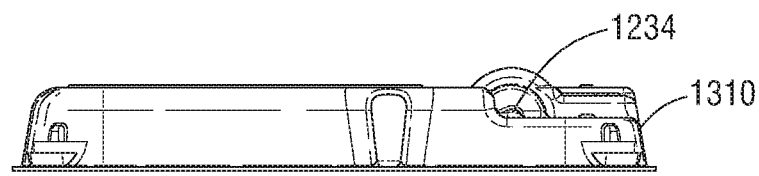
FIG. 18 is an elevation view of side 18-18 of the assembled packaging system of FIG. 14A.

As depicted in FIGS. 12, 14A and 14B, the structure of the valve cover 1210 differs from the valve cover 600 described above in reference to FIGS. 9 and 10 in certain respects. In the embodiment depicted in FIGS. 12, 14A and 14B, the valve cover 1210 can comprise a flared end open end 1212 that permits the ingress of the hydrating fluid for the prosthetic valve and an opposing securing end 1214 that provides a point of attachment to the distal end of the delivery system 1200.

The valve cover 1210 can further include a lock ring 1216 that can be slidable between a locked and unlocked position, as depicted by the double arrows in FIG. 12. In the locked position, the lock ring 1216 exerts a radially inward force around the securing end 1214 of the valve cover 1210 to fixedly secure the valve cover 1210 to the delivery system 1200. In the unlocked position, the radially inward force exerted by the lock ring 1216 around the securing end 1214 of the valve cover 1210 is released to permit removal of the delivery device 1200 from the valve cover 1210 after the hydrating, flushing, and loading of the prosthetic valve is completed.

As can be seen in FIGS. 12 and 14B, a spaced area 1116 is provided within the mounting surface 1112 of the cavity 1130 floor to permit the lock ring 1216 to freely slide between the locked and unlocked positions around the securing end 1214 while the valve cover 1210 itself remains fixed to the mounting surface 1112. Thus, it is not necessary to remove the valve cover 1210 from the tray 1100 in order to perform the steps required to prepare the prosthetic valve and delivery system 1200 for implantation.

The cavity 1130 can be dimensioned so as to at least accommodate a volume of hydrating fluid that is sufficient to submerge the prosthetic valve contained within valve cover 1210. The flared open end 1212 of the valve cover 1210 is also configured to permit immersion of the prosthetic valve in the hydrating fluid. When the cavity 1130 is filled with a sufficient volume of hydrating fluid to submerge the prosthetic valve, further filling of the cavity 1130 with the hydrating fluid will cause the fluid to fill an adjacent reservoir 1135, which is in fluid communication with the cavity 1130. The reservoir 1135 therefore can fulfill two functions—to provide a clear visual indication when a sufficient volume of hydrating fluid is provided in the cavity 1130 and to accommodate an excess of the hydrating fluid.

In addition to the cavity 1130, a ramp 1129 can be provided in a similar manner as described above with respect to FIGS. 1-6 in which the ramp 1129 can extend downwardly from the upper surface 1120 of the tray 1100 and down through an opening defined in the peripheral side wall adjacent the cavity 1130 floor. The angle of the ramp 1129 can be similarly provided so as to prevent overflow fluid from leaking out of the tray 1100.

The handle 1230 can be provided within the tray 1100, either attached to or detached from the delivery system 1200. FIGS. 12, 13, 14A, 14B and 19 depict the handle 1230 being attached to the delivery system 1200. The advantages to providing the handle 1230 in the attached state is that it eliminates a step in preparing the valve for implantation in the operating room. In one embodiment, the handle 1230 is battery-powered and the batteries (not shown) can be provided separately from the handle 1230 and also stored within a space 1160 within the tray 1100.

The tray 1100 also includes an engaging surface 1134 that provides a contoured and engaging fit with the handle 1230 so as to secure it within the tray 1100 from movement during storage, transportation, preparation and loading operation of the prosthetic valve. The handle 1230 comprises a side port 1232 and an end port 1234 to permit injection of the hydrating fluid through the catheter lumen and guide wire lumen, respectively, of the delivery system 1200. The tray 1100 can include a side port engaging surface 1132 to secure the side port 1232 during storage and transportation. The engaging surface 1134 of the tray 1100 can further include a channel and an opening in the raised side wall 1110 of the tray 1100 to permit access to the end port 1234 of the handle 1230 without removing the handle 1230 from the tray 1100. Thus, a syringe containing a hydrating fluid can be coupled to the end port 1234 of the handle 1230 without disengaging or removing the handle 1230 from the engaging surface 1134 of the tray 1100.

Figure 13:
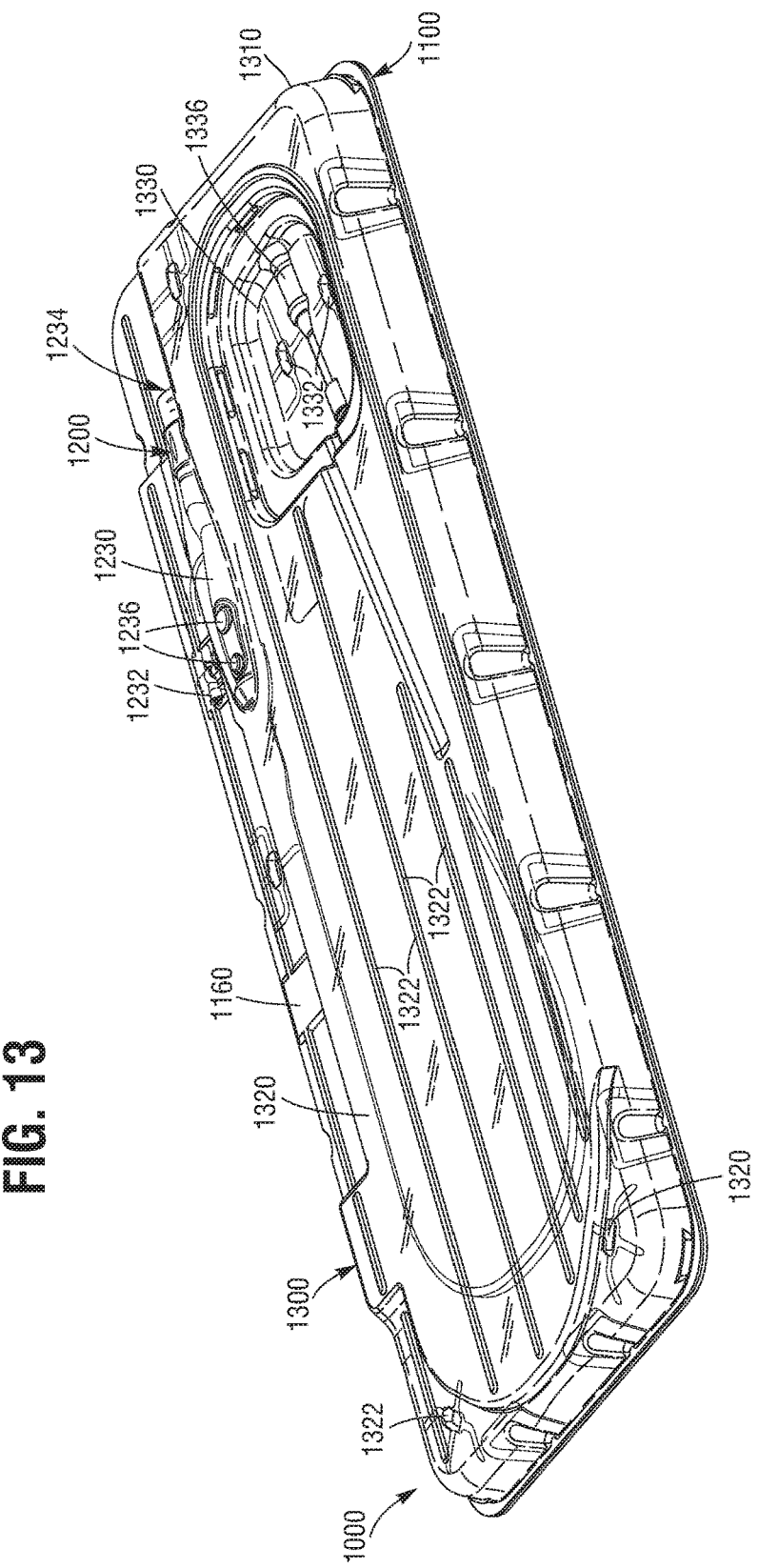
FIG. 13 is a perspective view of the packaging system with the tray, prosthetic valve delivery system and lid of FIG. 12 assembled together for storage and transportation.

FIGS. 12, 13 and 14A depict a lid 1300 provided in connection with the packaging system 1000. The lid 1300 can cover substantially the entirety of the upper surface 1120 and side walls 1110 of the tray 1100 so as to enclose the cavity 1130, reservoir 1135 and the delivery system 1200 that is removably affixed to the tray 1100. The lid 1300 can comprise a plurality of gas channels 1322 formed on the surface 1320 of the lid. The lid 1300 can also comprise a plurality of tabs 1332 to mate with corresponding recesses 1122 disposed on the tray 1100.

In one embodiment, the lid 1300 can include a contoured upper surface 1320 and side walls 1310 to provide a conforming fit to a substantial portion of the upper surface 1120 and side walls 1110, respectively, of the tray 1100. In one aspect of this embodiment, the lid 1300 is readily removable and is not frictionally fit with the tray 1100 and/or the delivery system 1200.

The handling of the packaging system 1000 containing the prosthetic valve and the associated delivery system 1200 can be the same as described above with reference to FIGS. 11A-11C. It is understood that the packaging system 1000 is provided in a sterile pouch and then sterilized by gas, such as by ethylene oxide or by gamma irradiation or electron beam irradiation, as described above and depicted in FIG. 11C. The sterile pouch can be gas impermeable and can comprise Tyvek material from DuPont. The packaging system 1000 contained with the sterile pouch can be provided within a second pouch, as depicted in FIG. 11B, which can be moisture impermeable, gas impermeable or both (e.g., a foil pouch). The packaging system 1000 provided in the two pouches can subsequently be provided in a box, as depicted in FIG. 11A for shipment. In accordance with one aspect of this embodiment, the cavity does not comprise a liquid or a preservative solution.

As indicated above, the exemplary steps for preparing and assembling the prosthetic valve and delivery system 1200 using the packaging system 1000 differ from the steps described above in reference to FIGS. 11D-11I.

After the packaging tray 1000 is removed from its outer packaging (i.e., the sterile pouch, second pouch and box) and is transferred from the non-sterile field to the sterile field as described with reference to FIGS. 11A-11C, the lid 1300 is removed from the tray 1100. After removing the lid 1300, a hydrating fluid is poured into the cavity 1130 until the hydrating fluid begins to overflow into the adjacent reservoir 1135 to indicate complete filling of the cavity 1130 and immersion of the valve contained within the delivery capsule 1210. If needed, the handle 1230 is removed from the engaging surfaces 1134 to install the batteries (not shown). The handle 1230 is then returned to the engaging surface 1134 of the tray 1100.

Figure 19:
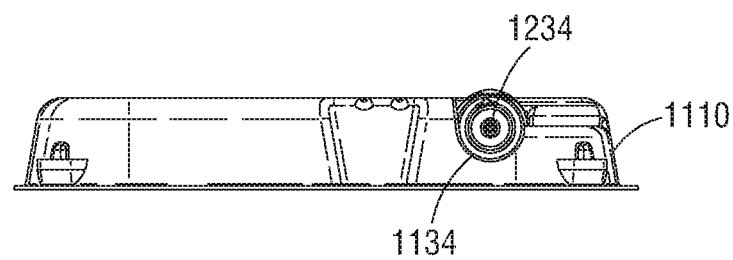
FIG. 19 is an elevation view of side 19-19 of the assembled packaging system of FIG. 14B.

A fluid can then be injected into the side port 1232 of the handle 1230 to flush the catheter lumen of the delivery system 1200. In one embodiment the fluid can be injected into the side port 1232 by a syringe containing the fluid. Once the flushing of the catheter lumen is complete, the loading of the heart valve can be performed by pressing the button 1236 to actuate the loading of the heart valve within the delivery sheath. After the loading is complete, a fluid can be injected into the end port 1234 of the handle 1230 to flush the guide wire lumen of the delivery system 1200. As can be seen in FIG. 19, the end port 1234 of the handle 1230 can be accessed by the syringe without removing the handle 1230 from the tray 1100. Thus, it is understood that during flushing and loading operations, the delivery capsule 1210 and the handle 1230 can remain fixed within the tray 1100.

After the flushing and the loading operations have been completed, the delivery system 1200 can finally be removed from the tray 1100. The removal of the delivery system 1200 can be accomplished by disengaging the handle 1230 from the engaging surface 1134, sliding the lock ring 1216 from the locked position to the unlocked position to release the radial pressure of the securing end 1214 onto the catheter portion 1220, and sliding the distal end of the delivery system 1200 out of the valve cover 1210.

In all of the embodiments described herein and in one optional aspect, the delivery system is packaged within the tray and the cavity does not comprise a liquid or a preservative solution until the hydrating solution is added during the process of preparing the valve for implantation. Thus, the valve that is housed within the cavity can be stored and transported in dry storage.

It is to be understood that the detailed description and specific examples, while indicating preferred embodiments of the present disclosure, are given by way of illustration and not limitation. Many changes and modifications within the scope of the present disclosure may be made without departing from the spirit thereof, and the disclosure includes all such modifications.

The invention claimed is:

1. A packaging system for storing a prosthetic valve and an elongated delivery system in a non-fluid environment, the packaging system comprising:
 a tray for securing both a prosthetic valve and an elongated delivery system; and
 a valve cover, wherein the prosthetic valve is maintained in a compressed state inside the valve cover and around a distal portion of the elongated delivery system and the valve cover is removable from the prosthetic valve and the delivery system, the tray including
  a cavity comprising an open end, a floor, and a peripheral side wall defining a depth of the cavity, the cavity sized and shaped to house the valve cover and the prosthetic valve;
  a mounting surface to removably couple the valve cover to the cavity floor;
  an engaging surface peripherally of the cavity and elevated above the cavity floor; and
  a ramp extending downwardly from the engaging surface and into the cavity through an opening defined in the peripheral side wall;
  wherein the engaging surface and the ramp are configured to secure at least a portion of the elongated delivery system externally of the cavity.

2. The packaging system of claim 1, wherein the prosthetic valve comprises a stent and a plurality of leaflets coupled to the stent, the plurality of leaflets comprising a biological tissue.

3. The packaging system of claim 1, wherein the engaging surface comprises a channel formed in the tray and shaped to accommodate the elongated delivery system and wherein the channel comprises tabs to resiliently engage the elongated delivery system within the channel.

4. The packaging system of claim 1, wherein the ramp is angled downwardly from the engaging surface to the floor of the cavity.

5. The packaging system of claim 4, wherein the ramp is provided at an angle of about 4 degrees to about 10 degrees relative to a horizontal plane bisecting the tray.

6. The packaging system of claim 1, further comprising a lock configured to be removably coupled to one or both of the valve cover and the distal portion of the elongated delivery system.

7. The packaging system of claim 1, further comprising:
 a lid removably coupled to the tray and partially enclosing the open end of the cavity.

8. The packaging system of claim 6, wherein the lock comprises a first end and a second end, wherein the first end is removably coupled to one or both of the valve cover and the distal portion of the elongated delivery system.

9. The packaging system of claim 8, wherein the second end is configured to protrude externally of the cavity through an aperture disposed on the lid, the second end being sized or shaped to prevent it from being passed through the aperture.

10. The packaging system of claim 8, wherein second end is fixed to or integrated with the lid.

11. The packaging system of claim 8, wherein removing the lid also removes the first end of the lock from the one or both of the valve cover and the elongated delivery system.

12. The packaging system of claim 1, wherein the valve cover comprises an internal cavity to house a nose piece, the prosthetic valve and part of the distal portion of the elongated delivery system.

13. The packaging system of 12, further comprising a lock that is removably coupled to both the valve cover and the distal portion of the elongated delivery system, wherein a first end of the lock is positioned to maintain a separation between the nose piece and the prosthetic valve.

14. The packaging system of claim 1, wherein the valve cover comprises wings extending laterally from opposing sides of the valve cover and wherein the wings are configured to couple the mounting surface disposed from the cavity floor.

15. The packaging system of claim 14, wherein the mounting surface is one of a pair of protrusions or a pair of recesses that are configured to mate with corresponding features of the wings, wherein the corresponding features of the wings are the other of the pair of protrusions or the pair of recesses and wherein the wings and the mounting surface are in resilient snap-fit engagement.

16. The packaging system of claim 1, wherein the cavity further comprises a fill line disposed from the cavity peripheral side wall between the floor and the open end.

17. The packaging system of claim 1, wherein a free segment of the elongated delivery system externally of the cavity is not in direct physical contact with the tray and wherein a space is provided around the free segment to permit a user's hand to grasp the free segment and lift at least a portion of the elongated delivery system on both sides of the free segment out of engagement with the tray.

18. The packaging system of claim 1, wherein the proximal end of the elongated delivery device is engaged within a periphery of the tray and wherein the tray comprises a support surface for maintaining the proximal end of the elongated delivery system in position for coupling the proximal end with a handle when the proximal end is disengaged from and extends externally away from the periphery of the tray.

19. The packaging system of claim 1, wherein the mounting surface resiliently engages at least a portion of an external surface of the valve cover.

20. The packaging system of claim 1, wherein the valve cover comprises a flared open end, an opposing securing end, and a lock ring mounted slidably around the securing end between a locked position and an unlocked position.

21. The packaging system of claim 20, wherein in the locked position, the lock ring exerts a radially inward force around the securing end of the valve cover to secure the valve cover onto the delivery system and wherein in the unlocked position, the radially inward force exerted by the lock ring is released to permit removal of the delivery device from the valve cover.

22. The packaging system of claim 21, wherein the lock ring is housed within a spaced area of the mounting surface on the cavity floor to permit the lock ring to slide between the locked and the unlocked positions, wherein the mounting surface resiliently engages at least a portion of an external surface of the valve cover.

23. The packaging system of claim 7, wherein the lid completely encloses the upper surface of the tray.

24. The packaging system of claim 1, further comprising a handle attached to the delivery system and packaged within the tray.

25. The packaging system of claim 1, further comprising a reservoir in fluid communication with the cavity.

26. A method for preparing a prosthetic valve and its associated delivery system for implantation of the prosthetic valve in a patient, the method comprising:
   (a) obtaining a tray, the tray comprising a prosthetic valve in a first compressed state inside a valve cover and coupled to an elongated delivery system, the valve cover being removable from the prosthetic valve and the delivery system, and the tray including
      a cavity comprising an open end, a floor, and a peripheral side wall defining a depth of the cavity, the cavity sized and shaped to house the valve cover, the prosthetic valve and at least part of a distal portion of the elongated delivery system;
      a mounting surface to substantially immobilize and maintain the valve cover and the prosthetic valve within the cavity;
      an engaging surface peripherally of the cavity and elevated above the cavity floor; and
      a ramp extending downwardly from the engaging surface and into the cavity through an opening defined in the peripheral side wall;
      wherein the engaging surface and the ramp are configured to secure at least a portion of the elongated delivery system externally of the cavity;
   (b) at least partially filing the cavity with a first hydrating fluid to completely immerse the prosthetic valve;
   (c) allowing the prosthetic valve to soak in the first hydrating fluid for a period of time;
   (d) flushing the elongated delivery system by delivering a second hydrating fluid into a proximal end of the elongated delivery system and causing the second hydrating fluid to pass through a lumen extending through the elongated delivery system and out of the distal portion of the elongated delivery system; and
   (e) causing the prosthetic valve to be loaded into a lumen of a delivery sheath associated with the elongated delivery system while the prosthetic valve is coupled to the cavity floor via the mounting surface;
      wherein the loading is performed by causing the delivery sheath move axially over the prosthetic valve;
      wherein the delivery sheath compresses and contains the prosthetic valve within a lumen of the delivery sheath in a second compressed state; and
      wherein a diameter of the prosthetic valve in the first compressed state is larger than a diameter of the prosthetic valve in the second compressed state;
   (f) removing the elongated delivery device with the prosthetic valve loaded into the lumen of the delivery sheath from the tray, including removing the distal portion of the delivery system from the valve cover and disengaging the prosthetic valve from the mounting surface; and
wherein (a) through (e) are performed while the prosthetic valve is substantially immobilized and maintained within the cavity.

* * * * *